(12) United States Patent
Zeng

(10) Patent No.: US 12,319,661 B2
(45) Date of Patent: Jun. 3, 2025

(54) POLYCYCLIC COMPOUND

(71) Applicant: EUTEC NEW MATERIALS TECHNOLOGY (SUZHOU) CO., LTD., Jiangsu (CN)

(72) Inventor: Yufeng Zeng, Jiangsu (CN)

(73) Assignee: EUTEC NEW MATERIALS TECHNOLOGY (SUZHOU) CO., LTD. (CN)

( * ) Notice: Subject to any disclaimer, the term of this patent is extended or adjusted under 35 U.S.C. 154(b) by 967 days.

(21) Appl. No.: 17/311,987

(22) PCT Filed: Mar. 13, 2019

(86) PCT No.: PCT/CN2019/077919
§ 371 (c)(1),
(2) Date: Sep. 7, 2021

(87) PCT Pub. No.: WO2020/118933
PCT Pub. Date: Jun. 18, 2020

(65) Prior Publication Data
US 2022/0017474 A1    Jan. 20, 2022

(30) Foreign Application Priority Data
Dec. 10, 2018   (CN) .......................... 201811501755.4

(51) Int. Cl.
| | | |
|---|---|---|
| C07D 249/20 | (2006.01) | |
| C07D 239/62 | (2006.01) | |
| C07D 401/12 | (2006.01) | |
| C07D 403/10 | (2006.01) | |
| C07D 403/12 | (2006.01) | |
| C07D 405/06 | (2006.01) | |
| C07D 405/10 | (2006.01) | |
| C07D 405/12 | (2006.01) | |
| C07D 409/12 | (2006.01) | |
| C07D 413/12 | (2006.01) | |
| C07D 417/12 | (2006.01) | |

(52) U.S. Cl.
CPC ......... *C07D 249/20* (2013.01); *C07D 239/62* (2013.01); *C07D 401/12* (2013.01); *C07D 403/10* (2013.01); *C07D 403/12* (2013.01); *C07D 405/06* (2013.01); *C07D 405/10* (2013.01); *C07D 405/12* (2013.01); *C07D 409/12* (2013.01); *C07D 413/12* (2013.01); *C07D 417/12* (2013.01)

(58) Field of Classification Search
CPC .................................................... C07D 249/20
USPC .......................................................... 544/92
See application file for complete search history.

(56) References Cited

FOREIGN PATENT DOCUMENTS

WO    2005/066141 A1  *  7/2005

* cited by examiner

*Primary Examiner* — Taofiq A Solola

(57) ABSTRACT

Novel polycyclic compounds, synthesis methods and applications thereof are provided. The compound comprise a plurality of carbocyclic and/or heterocyclic structures having at least one group that emits visible light or fluorescence and at least one ultraviolet and/or visible (blue) light absorbing group covalently bonded to provide stability. The compounds can be used as a light conversion agent, dye, pigment, fluorescence agent, ultraviolet light or blue light absorber, and is applied to optical film, agricultural film, optical disk (disc), optical lens, goggles, skin care, makeup, lighting, coatings, adhesives, light stabilizers, or panels.

4 Claims, 2 Drawing Sheets

| | peak/valley | wavelength (nm) | Abs |
|---|---|---|---|
| 1 | peak | 442.00 | 1.063 |
| 2 | peak | 337.50 | 0.333 |
| 3 | peak | 244.50 | 0.277 |
| 1 | valley | 375.00 | 0.131 |
| 2 | valley | 261.00 | 0.120 |

POLYCYCLIC COMPOUND

FIELD

The present invention relates to novel polycyclic compounds, their synthesis and applications. The compound of the present invention includes one or more carbocyclic and/or heterocyclic structures, which has a group that emits visible light or fluorescence, and is covalently bonded with at least one ultraviolet and/or blue absorbing group to provide stability. The compounds of the present invention can be used as light conversion agents, dyes, pigments, fluorescent agents, ultraviolet light or blue light absorbers, and are used in optical films, agricultural films, optical discs, optical lenses, goggles, skin care, color cosmetics, lighting, coatings, adhesives Agents, light stabilizers, or panels and other products.

BACKGROUND

At present, organic compounds with light-emitting properties, including dyes, pigments, or fluorescent substances, are widely used in agriculture, electronics industry, and medicine. For example, optical recording media such as light conversion agents or optical discs.

In agriculture, adding a light conversion agent to agricultural film can convert ultraviolet light of sunlight or short-wavelength blue light into light that is useful to plants. Red light is the most important light for the growth of crops, which can promote the increase of crop production. For example, in the early stage of heading for Chinese cabbage, red light can promote the formation of leafy vegetables, but excessive blue light can inhibit it (Journal of Agricultural Machinery, ISSN: 1019-0430, Vol 8 (2), 1999 June, p. 63-74). In addition, there have been documents published that the commercial organic light conversion agent, RL1000 (Compound A, BASF), used in agricultural film can absorb ultraviolet light to reduce pests such as aphids and emit visible light (about 635 nm) that is beneficial to plants. Unfortunately, the stability is quite insufficient (CN 100500754 C).

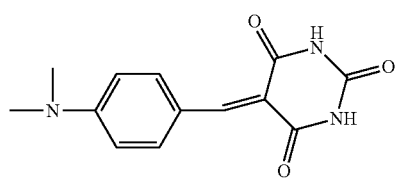

(A)

Generally, organic compounds are prone to degradation when used outdoors, such as organic light conversion agent, RL1000. Therefore, improving the stability is an important indicator for the improvement of the light conversion agent.

In addition, known optical recording media, such as optical discs, are made by irradiating a laser beam to an organic dye in the recording layer. In a short period of time, the laser will be converted into heat, causing thermal deformation of the recording layer, for example, into a molten state. According to the difference in the reflectance of light between the deformed part and the non-deformed part, information is recorded. As the process of converting laser energy into heat, the local high temperature can reach 250° C. or above. Therefore, the melting point and thermal stability of the dye become important factors. There was a document that disclosed the organic compound (B) for use in optical recording media (JP 3876970 B2). But the melting point is low and the stability is poor.

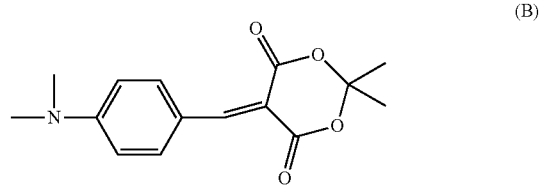

(B)

In addition, it is known that ultraviolet light and/or blue light irradiation is an important factor that causes degradation of organic materials, such as agricultural films or optical recording media. Adding anti-blue and/or anti-ultraviolet agents can increase the shelf life of agricultural films or optical discs. However traditional anti-blue light agents can only achieve the functions of anti-bluelight and anti-ultraviolet long wavelength (UVA) at the same time. If you need to prevent blue light, UVA and UVB (short ultraviolet wavelength) at the same time, you must additionally add UVB. This is not conducive to industrial utilization. Therefore, the development of compounds that absorb ultraviolet light (UVA+UVB) and blue light has become the goal of the industry.

In summary, to increase the stability of dyes for luminescent recording media, light conversion agents, and compounds that absorb ultraviolet light (UVA+UVB) and blue light are the goals of the industry.

SUMMARY

To develop high-stability organic dyes, light conversion agents, or compounds that absorb ultraviolet light (UVA+UVB) and blue light has always been the goal of the industry. To achieve this goal, the inventors deliberately designed novel polycyclic compounds of formula (1) and formula (2).

The design concept of the compounds of formula (1) and formula (2) of the present invention is to covalently bond dyes or light-converting substances with substances that absorb ultraviolet light or/and blue light. The compound of formula (1) or formula (2) designed by this new concept greatly increases the stability of the original organic dyes or light conversion agents. Because the range of blue and ultraviolet light (UVA+UVB) absorption is increased, at the same time, stability of protected organic materials increases.

This may also be because the covalently bonded ultraviolet light absorbing groups provide stability to the light conversion agent itself at close distances within the molecule. Furthermore, the ultraviolet light absorbing group also provides stability to the protected organic . . . material around the molecule, such as agricultural film. As a result of the dual effect, the durability or stability of the agricultural film is greatly increased.

The organic light conversion agent A (RL1000, BASF) currently used in agricultural film can emit orange-red light under sunlight. But its light stability is insufficient. In the use of outdoor PE agricultural film, RL1000 can only maintain the stability of two seasons.

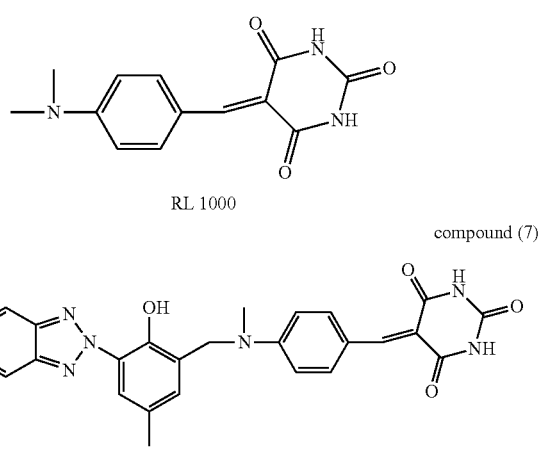

RL 1000 compound (7)

After compound A (RL1000) covalently bonding with a benzotriazole, MP259 (compound 7) is obtained, which can maintain the outdoor stability of the PE agricultural film for more than three seasons (example 43).

Another example is the aforementioned organic dye compound (B) applied to optical recording media, which possesses a melting point of 175° C. After covalently bonding with a benzotriazole, the melting point of compound (B) rose to 224° C. (example 41). This is an important and unexpected improvement.

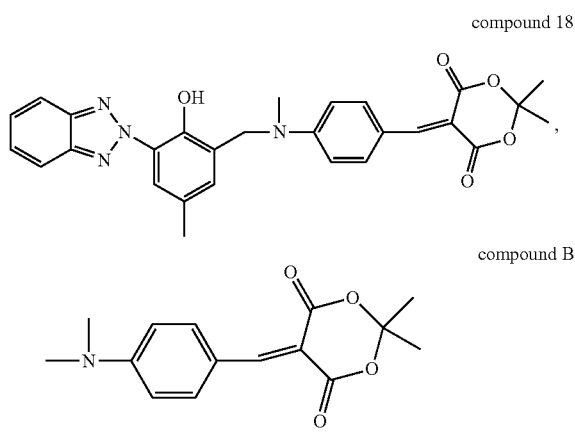

compound 18 compound B

Because the organic dye of the optical disc absorbs the laser and converts it into heat, it will cause local high temperature (250° C. or above). After compound (B) is covalently bonded with benzotriazole, not only the melting point and thermal stability are improved, but the ultraviolet light (UVA+UVB) absorption capacity provided by benzotriazole can also increase the storage life of the optical disc.

Preferably, the compounds of the present invention increase stability without affecting the original luminescence properties of organic dyes or light conversion agents.

More preferably, the structure of $R_1$ to $R_3$ in the compound of formula (1) or formula (2) is designed to increase or decrease the conjugability, therefore can increase or decrease the original luminescence properties of the organic dye or light conversion agent. For example, the compound (19) of example 11, on the one hand, has increased conjugation compared with the compound (18), and on the other hand, it also increases the wavelength of visible light absorption. The application field can also be extended from dyes to other fields, such as agricultural film. In addition, the highly stable compound (7) can also be applied to the red laser (640 nm) commonly used in DVD-R discs in addition to the application in agricultural films.

Furthermore, the compounds of the present invention can also be applied as ultraviolet light and/or blue light absorbers. Due to the luminescent properties of the compound of the present invention, it can be used as a special ultraviolet light absorber and/or blue light absorber. Traditional anti-blue light absorbers can only absorb ultraviolet light (UVA) and blue light. The compound of the present invention has a wide range of ultraviolet light (UVA+UVB) absorption, so it can absorb ultraviolet light (UVA+UVB) and blue light at the same time without adding additional ultraviolet (UVB) absorbers, and fully protect the human body, polymers or other organic materials.

The compound provided by the present invention is a polycyclic compound with a structure represented by formula (1) or formula (2).

$$A\text{-}R_1\text{—}B\text{—}R_2\text{—}C\text{—}R_3\text{-}D \tag{1}$$

$$A\text{-}R_1\text{—}B\text{—}R_2\text{-}D\text{-}R_3\text{—}C \tag{2}$$

In the present invention, A, B, C, and D between the formula (1) and formula (2) are the same, and the difference lies only in the order of the C ring and the D ring. Therefore compound of formula (1) and formula (2) compliance with the requirements of invention unity.

The compound of formula (1) or formula (2) of the present invention is characterized by comprising at least one visible light or fluorescence emitting group and at least one additional ultraviolet light absorbing group.

$R_2$—C—$R_3$-D or $R_2$-D-$R_3$—C is a visible light emitting group or a fluorescence emitting group; A-$R_1$—B is an ultraviolet light absorbing group;

$R_1$ to $R_3$ are single bond or/and any divalent linking group, preferably, $R_1$ is a bond or any divalent linking group, more preferably, $R_1$ is both a bond and a divalent linking group, For example, A-$R_1$—B is 9-hydrocarbazole or dibenzothiophene; A, B, and C are unsubstituted 5~7 membered rings, for example, benzene ring, or 5~7 membered rings substituted with $R_4$. A, B, and C can be unsubstituted benzocarbocyclic ring or benzocarbocyclic ring substituted with $R_4$.

A, B, and C are unsubstituted nitrogen containing 5~7 membered heterocyclic ring, or nitrogen containing benzoheterocycles substituted with $R_4$. The nitrogen on nitrogen-containing heterocycles may be replaced by other heteroatoms. Nitrogen-containing 5~7 membered benzoheterocycles may refer to the fusion of a benzene ring and a nitrogen-containing 5~7 membered heterocycle.

D is an unsubstituted or substituted 5~7 membered heterocyclic ring or a benzo-heterocyclic ring composed of carbon, nitrogen, oxygen, and sulfur atoms, wherein the substituent of the ring on carbon atoms are selected from one or more hydrogen, hydroxyl, oxo, thioxo, thiol, amino, imino, $C_1$~$C_8$ linear or branched alkyl or $R_4$. The substituent of the ring on nitrogen atom is selected from one or more hydrogen, hydroxyl, oxo, and linear or branched $C_1$~$C_8$ alkyl.

$R_4$ is one or more substituents (in the structural formula of the present invention, the substitution of $R_4$ or other substituents at an indefinite position refers to any position on the ring. For example, when the structural formula shows that the bonding of $R_4$ on the ring is at between two atoms, it refers to the bonding of $R_4$ at any position on the ring). $R_4$ is independently selected from hydrogen, halogen, hydroxyl, amino, nitro, cyano, linear or branched $C_1$~$C_{18}$ alkyl, alkenyl or alkoxy, substituted or unsubstituted phenyl, $SR_5$, $SO_2R_5$, $SO_3R_5$, $COOR_5$, $COR_5$, $OCOR_5$, $C(O)NR_6R_7$, $SO_2NR_6R_7$, or $NR_6R_7$, wherein, $R_5$, $R_6$, and $R_7$ are each independently selected from hydrogen, or linear or branched $C_1$~$C_8$ alkyl groups. $R_4$ and adjacent $R_4$, or adjacent ring, can together form 3~6 atom fused carbocyclic or fused heterocyclic ring. Preferably, the fused heterocyclic ring containing one or more 3~6 atoms of C, N, O, S. Preferably, the halogen is chlorine.

Preferably, $R_1$ to $R_3$ is a bond, or a chain consisting of 1-10 groups selected from the following groups: —O—, —S—, —C(=O)—, —COO—, —C(=S)—, —C(=N—$R_{13}$)—, —N($R_{13}$)—, —C($R_{14}$)($R_{15}$)—, —C($R_{16}$)=, —C≡, —C($R_{17}$)=C($R_{18}$)—, or -Ph-. $R_{13}$~$R_{18}$ is one or more, and each is independently selected from hydrogen, halogen, hydroxyl, unsubstituted or halogen-substituted linear or branched $C_1$~$C_6$ alkyl (preferably, $C_1$~$C_4$ alkyl), and unsubstituted phenyl or phenyl substituted with halogen or $C_1$~$C_6$ alkyl (preferably, $C_1$~$C_4$ alkyl). Ph is phenyl which is unsubstituted or substituted by halogen, OH group or linear or branched $C_1$~$C_6$ alkyl (preferably, $C_1$~$C_4$ alkyl). Preferably, halogen is chlorine.

A is selected from:

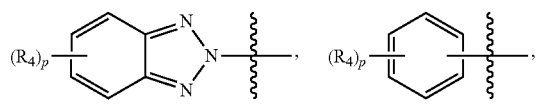

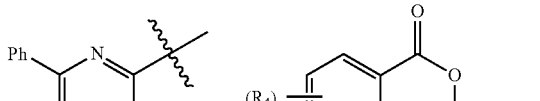

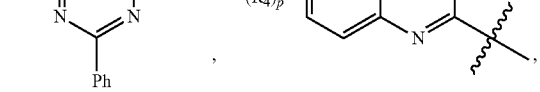

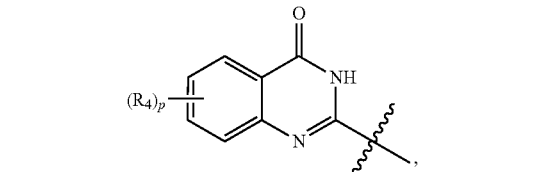

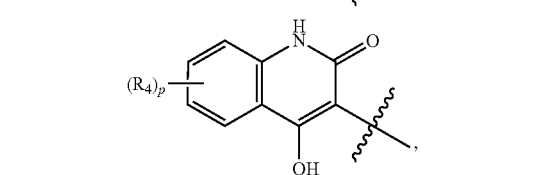

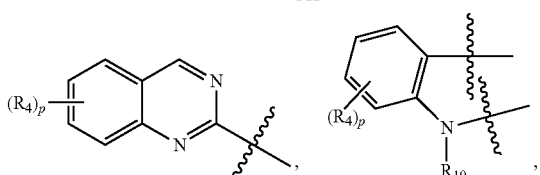

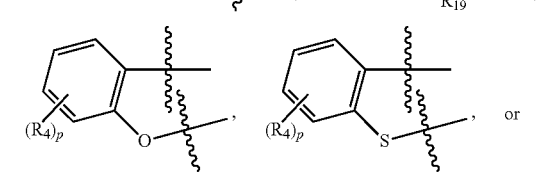

-continued

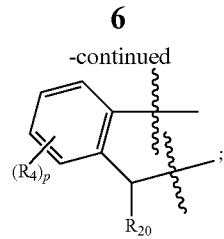

A is substituted by one or more $R_4$ or Ph. Wherein, p=0~3, preferably, p=0~2;

$R_4$ is one or more substituents, and each is independently selected from hydrogen, halogen, nitro, cyano, linear or branched $C_1$~$C_8$ alkyl, alkenyl or alkoxy, $SR_5$, $SO_2R_5$, $COOR_5$, $COR_5$, $C(O)NR_6R_7$, or $NR_6R_7$, wherein, $R_5$, $R_6$, and $R_7$ are each independently selected from hydrogen, linear or branched $C_1$~$C_8$ alkyl group, preferably, $R_5$, $R_6$, and $R_7$ are hydrogen or linear or branched $C_1$~$C_4$ alkyl. Preferably, the halogen is chlorine. Ph is unsubstituted or substituted phenyl, preferably, the substituent is halogen, hydroxyl, $C_1$~$C_6$ alkoxy (preferably, $C_1$~$C_4$ alkoxy) or $C_1$~$C_6$ alkyl (preferably, $C_1$~$C_4$ alkyl) substituted phenyl, preferably, halogen is chlorine. $R_{19}$~$R_{20}$ are one or more, and each is independently selected from hydrogen, linear or branched $C_1$~$C_6$ alkyl (preferably, $C_1$~$C_4$ alkyl), unsubstituted or substituted phenyl, preferably, the substituent is halogen or a linear or branched $C_1$~$C_6$ alkyl (preferably, $C_1$~$C_4$ alkyl).

B is selected from:

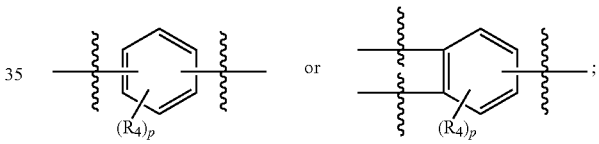

C is selected from:

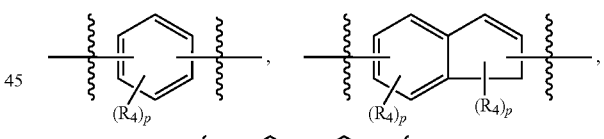

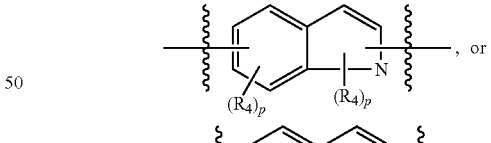

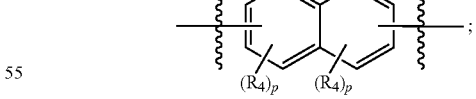

D is selected from:

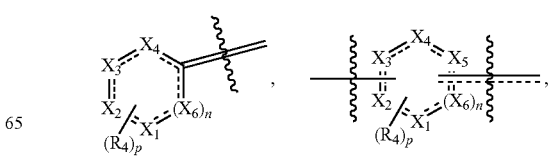

-continued

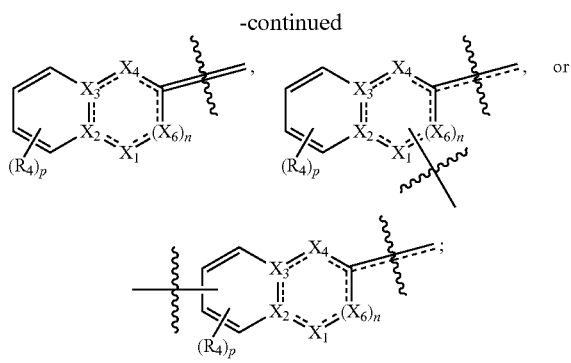

Wherein, p=0~3, preferably, p=0~2; n=0~1; $X_1$ to $X_6$ are each independently selected from C=O, C=S, C=N—$R_8$, N, $NR_9$, C, O, S, $CR_{10}$, $CR_{11}R_{12}$, $CNR_{11}R_{12}$, or $CR_{10}NR_{11}R_{12}$, wherein, $R_8$~$R_{12}$ are one or more, and each independently selected from hydrogen, linear or branched $C_1$~$C_8$ alkyl or alkenyl, linear or branched $C_1$~$C_6$ alkyl (preferably, $C_1$~$C_4$ alkyl) or unsubstituted or phenyl substituted by halogen; D is unsubstituted or substituted by $R_4$ and is connected to the outside of the ring via 1 to 2 double bonds or single bonds. Preferably, D is connected to the outside of the ring via a double bond. Preferably, the halogen is chlorine.

More preferably, $R_1$ to $R_3$ are a bond, or/and a chain consisting of 1~6 units selected from the following groups:—O—, —C(=O)—, —COO—, —N($R_{13}$)—, —C($R_{14}$)($R_{15}$)—, —C($R_{16}$)—, —C($R_{17}$)=C($R_{18}$)—, and -Ph-. Wherein, $R_{13}$~$R_{18}$ are one or more groups, and each is independently selected from hydrogen, unsubstituted or halogen-substituted linear or branched $C_1$~$C_6$ alkyl (preferably, $C_1$~$C_4$ alkyl), unsubstituted phenyl or phenyl substituted with halogen or $C_1$~$C_6$ alkyl (preferably, $C_1$~$C_4$ alkyl). Ph is unsubstituted or substituted by halogen, OH group or $C_1$~$C_6$ alkyl (preferably, $C_1$~$C_4$ alkyl). Preferably, halogen is chlorine.

A is selected from:

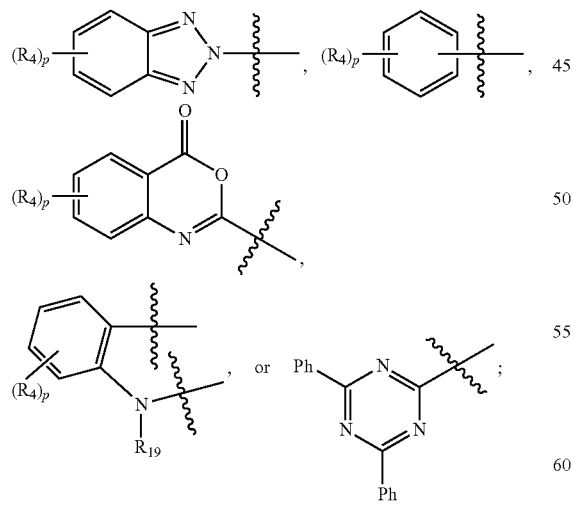

p = 0~2;

$R_4$ is one or more substituents, and each is independently selected from hydrogen, halogen, nitro, cyano, linear or branched $C_1$~$C_8$ alkyl, alkenyl or alkoxy, $SR_5$, $SO_2R_5$, $COOR_5$, $COR_5$, $C(O)NR_6R_7$, or $NR_6R_7$, wherein, $R_5$, $R_6$, and $R_7$ are each independently selected from hydrogen, linear or branched $C_1$~$C_8$ alkyl group, preferably, $R_5$, $R_6$, and $R_7$ are hydrogen or linear or branched $C_1$~$C_4$ alkyl group, Preferably, the halogen is chlorine. Ph is an unsubstituted or a substituted phenyl group, preferably, the substituent is hydrogen, halogen, OH group, $C_1$~$C_6$ alkoxy (preferably, $C_1$~$C_4$ alkoxy) or $C_1$~$C_6$ alkyl (preferably, $C_1$~$C_4$ alkyl) substituted phenyl. Preferably, halogen is chlorine;

B is selected from:

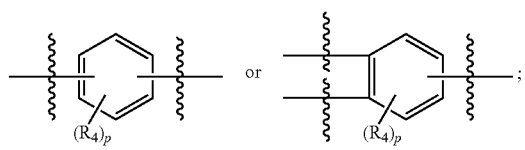

C is selected from:

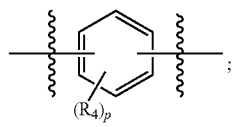

D is selected from:

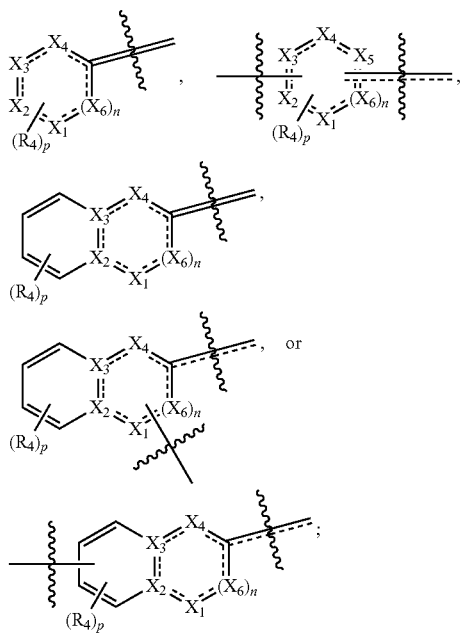

wherein, when n=0, $X_1$ is selected from C=O, C=S. $X_2$, $X_3$ and $X_4$ are each independently selected from C=O, C=S, C=N—$R_8$, C—$NR_{11}R_{12}$, N, $NR_9$, C, O, S, $CR_{10}$, or $CR_{11}R_{12}$;

When n=1, $X_4$ and $X_6$ are each independently selected from C=O, C=S. $X_1$, $X_2$, and $X_3$ are each independently selected from C=O, C=S, C=N—$R_8$, N, $NR_9$, C, O, S, $CR_{10}$, $CR_{11}R_{12}$, or C—$NR_{11}R_{12}$; $R_8$~$R_{12}$ are one or more, and are each independently selected from hydrogen, linear or branched $C_1$~$C_6$ alkyl (preferably, $C_1\text{~}C_4$ alkyl), unsubstituted or halogenated or $C_1\text{~}C_6$ alkyl group (preferably, the $C_1\text{~}C_4$ alkyl) substituted phenyl. D is unsubstituted or substituted by $R_4$ and is connected to the outside of the ring via 1 to 2 double bonds or single bonds. Preferably, D is connected to the outside of the ring via a double bond.

Most preferably, $R_2$ is a bond or —$(CHR_{21})q\ N(R_{22})$—, wherein $R_{21}$ and $R_{22}$ are each independently selected from hydrogen, linear or branched $C_1\text{~}C_8$ alkyl (preferably, $C_1\text{~}C_4$ alkyl), or unsubstituted phenyl or phenyl substituted with $C_1\text{~}C_6$ alkyl (preferably, $C_1\text{~}C_4$ alkyl); q=0~18, preferably, q=0~8, more preferably, q=0~4, especially good, q=0~2, the best, q=1;

D is selected from:

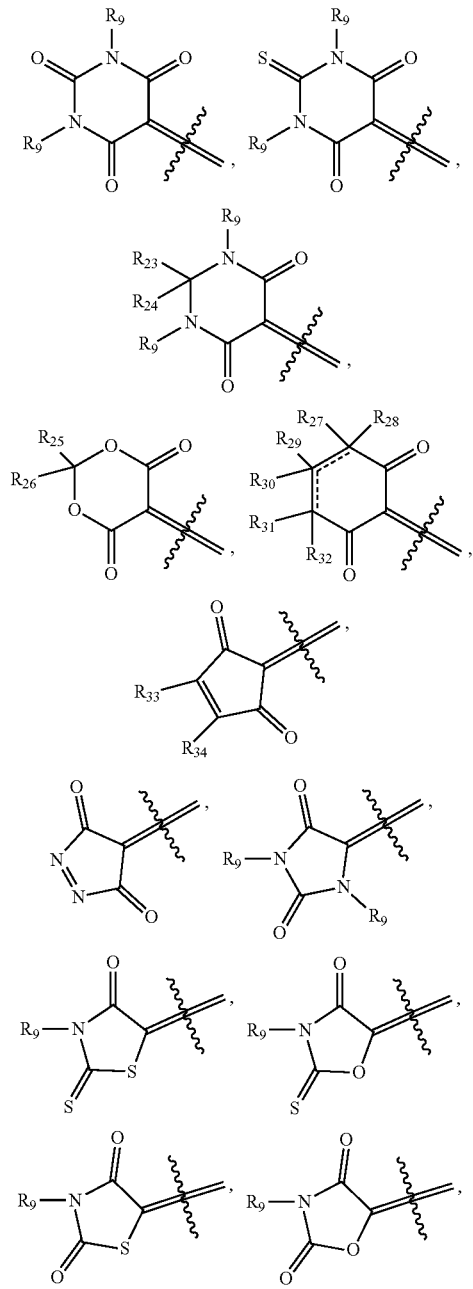

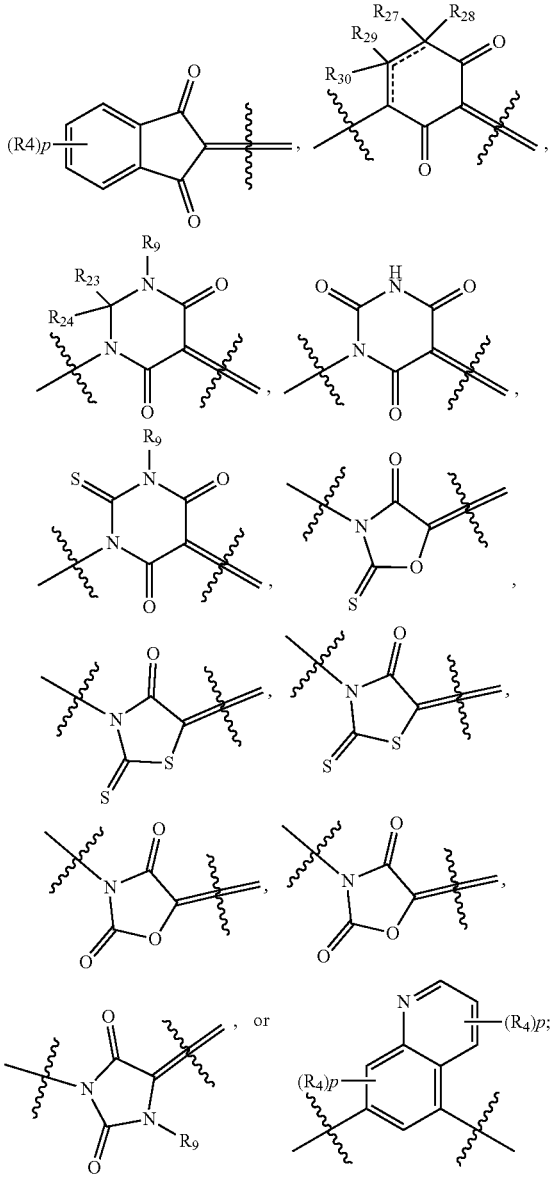

wherein $R^4$ is one or more substituents, and each is independently selected from hydrogen, halogen, linear or branched $C_1\text{~}C_8$ alkyl, alkenyl or alkoxy (preferably, $C_1\text{~}C_6$ or $C_1\text{~}C_4$ alkyl, alkenyl or alkoxy), $SR_5$, $SO_2R_5$, $COOR_5$, $COR_5$, $C(O)NR_6R_7$, or $NR_6R_7$, wherein, $R_5$, $R_6$, and Ry are each independently selected from hydrogen, or linear or branched $C_1\text{~}C_6$ alkyl group, preferably, $R_5$, $R_6$, and Ry are hydrogen or linear or branched $C_1\text{~}C_4$ alkyl group, Preferably, the halogen is chlorine. Ph is an unsubstituted or a substituted phenyl group, preferably, the substituent is hydrogen, halogen, OH group, $C_1\text{~}C_6$ alkoxy (preferably, $C_1\text{~}C_4$ alkoxy) or $C_1\text{~}C_6$ alkyl (preferably, $C_1\text{~}C_4$ alkyl) substituted phenyl, preferably, halogen is chlorine; p=0~2; preferably, p=0~1, particularly preferably, p=0; $R_9$, $R_{23}\text{~}R_{34}$ are selected from hydrogen, linear or branched $C_1\text{~}C_6$ alkyl (preferably, $C_1\text{~}C_4$ alkyl), unsubstituted phenyl or $C_1\text{~}C_6$ alkyl (preferably, $C_1\text{~}C_4$ alkyl) substituted phenyl.

Particularly preferably, A-R₁—B is selected from:

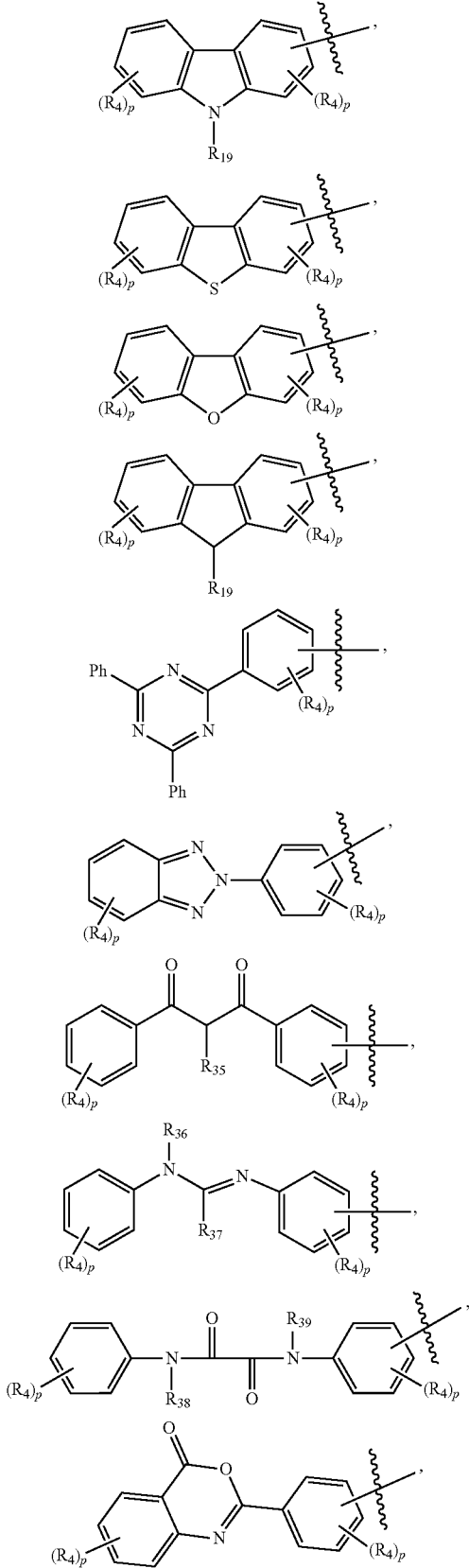

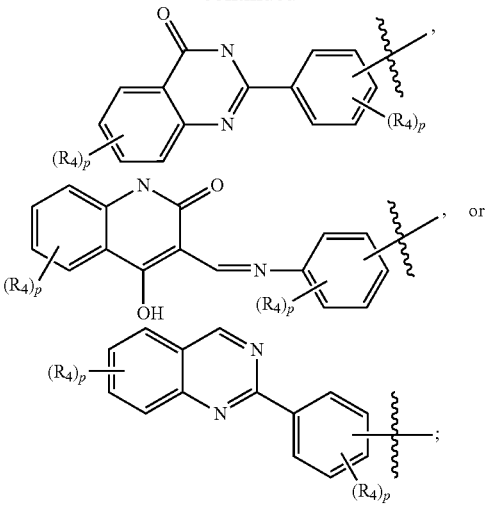

$R_4$ is one or more substituents, and each is independently selected from hydrogen, halogen, hydroxyl, amino, nitro, cyano, linear or branched $C_1$~$C_{18}$ alkyl, alkenyl or alkoxy, substituted or unsubstituted phenyl, $SR_5$, $SO_2R_5$, $SO_3R_5$, $COOR_5$, $COR_5$, $OCOR_5$, $C(O)NR_6R_7$, $SO_2NR_6R_7$, or $NR_6R_7$, wherein $R_5$, $R_6$, and $R_7$ are each independently selected from hydrogen, linear or branched $C_1$~$C_8$ alkyl (preferably, $C_1$~$C_4$ alkyl), or $R_4$ and adjacent $R_4$, or adjacent rings may together represent a 3~6 atom fused carbocyclic or fused heterocyclic ring, preferably a 3~6 atom fused heterocyclic ring containing C, N, O, S, preferably, the halogen is chlorine; p=0~2, preferably, p=0~1, more preferably, p=0.

$R_{19}$ and $R_{35}$~$R_{39}$ are one or more, and each independently selected from H, linear or branched $C_1$~$C_6$ alkyl (preferably, $C_1$~$C_4$ alkyl), unsubstituted or halogenated or $C_1$~$C_6$ alkyl (preferably, $C_1$~$C_4$ alkyl) substituted phenyl; Ph is unsubstituted phenyl or phenyl substituted by halogen, OH or $C_1$~$C_6$ alkyl (preferably, $C_1$~$C_4$ alkyl), preferably, the halogen is chlorine.

Very particularly preferably, the compound of formula (1) or formula (2) includes at least one visible light or fluorescent emitting group and at least one ultraviolet light absorbing group covalently linked, wherein the visible light or fluorescent emitting group is $R_2$—C—$R_3$-D $R_2$-D-$R_3$—C, selected from:

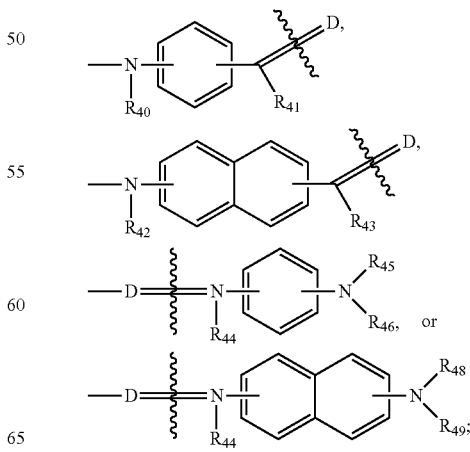

D selected from:
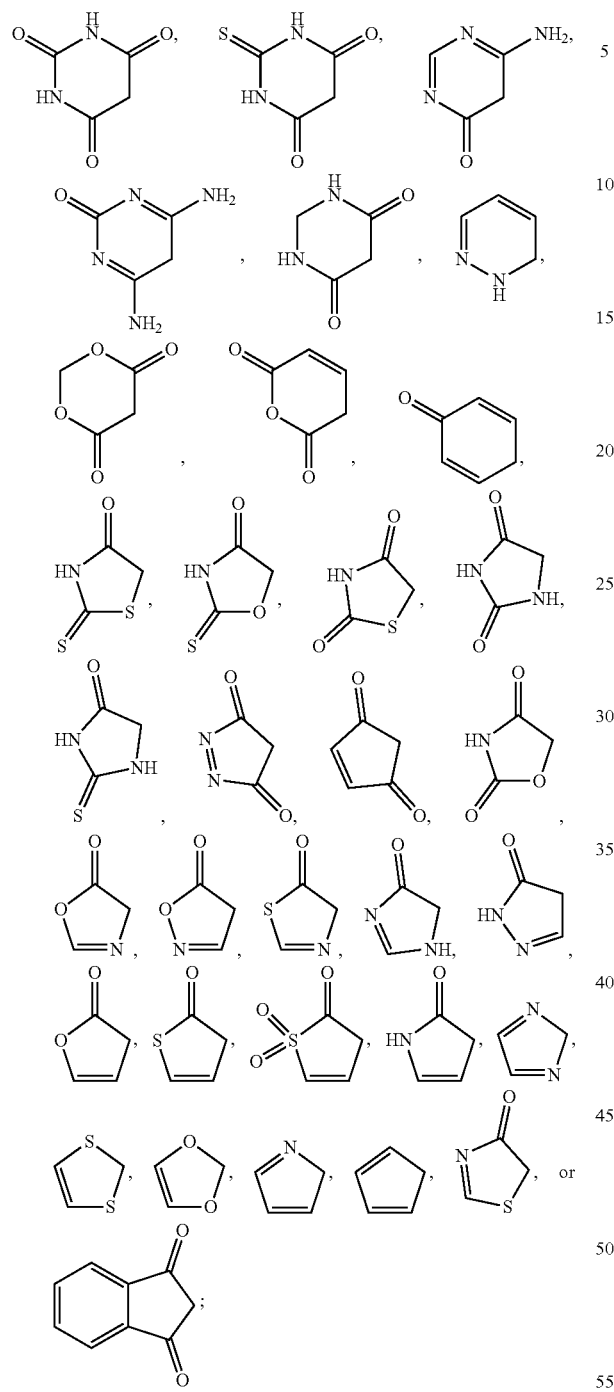
Wherein the ultraviolet light absorbing group is A-R$_1$—B, and is selected from:
Benzotriazole:
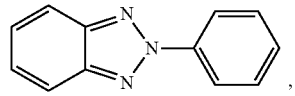
Triazine:
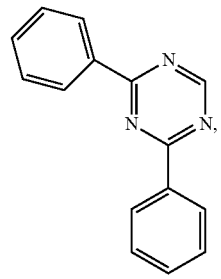
carbazole:
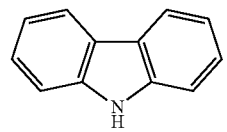
Oxanilide:
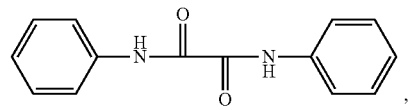
Benzoxazinone:
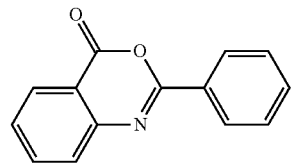
Quinazolinone:
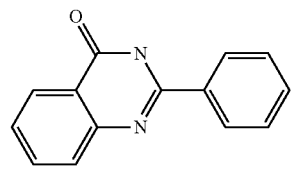
Dibenzoylmethane:
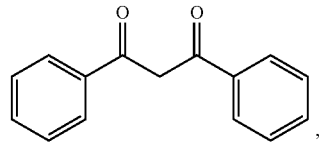
Phenylformamidine:
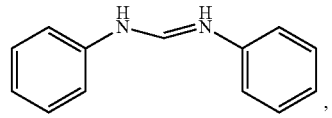
Azomethine:
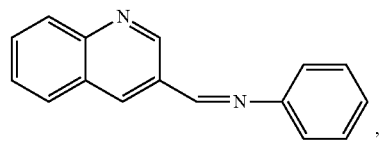

-continued

Quinazoline:

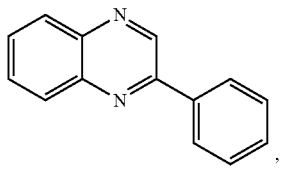,

Benzoic acid:

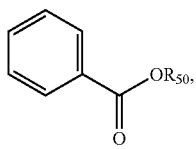,

Benzophenone:

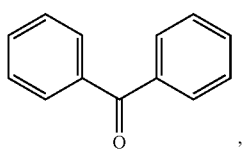,

Dibenzothiophene:

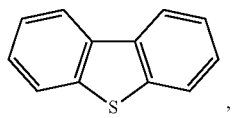,

Dibenzofuran:

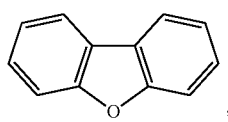,

Diphenyl sulfide:

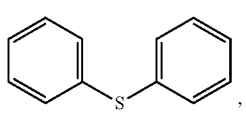,

Oxydibenzene:

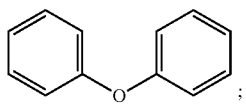;

wherein, the visible light emitting groups or the ultraviolet light absorbing groups are substituted by ($R_4$) p substituent, wherein p=0~3, preferably, p=0~1, particularly preferably, p=0. $R_4$ is a substituent, and each is independently selected from hydrogen, halogen, hydroxyl, amino, nitro, cyano, linear or branched $C_1$~$C_{18}$ alkyl, alkenyl or alkoxy, unsubstituted phenyl or phenyl substituted by one or more linear or branched $C_1$~$C_6$ alkyl or halogen, $SR_5$, $SO_2R_5$, $SO_3R_5$, $COOR_5$, $COR_5$, $OCOR_5$, $C(O)NR_6R_7$, $SO_2NR_6R_7$, or $NR_6R_7$, wherein $R_5$, $R_6$, and $R_7$ are each independently selected from hydrogen, linear or branched $C_1$~$C_8$ alkyl groups (preferably, $C_1$~$C_4$ alkyl); $R_4$ and adjacent $R_4$, or adjacent ring, together form 3~6 atom fused carbocyclic or fused heterocyclic ring. $R_{40}$~$R_{49}$ are the same or different and are each independently selected from hydrogen, linear or branched $C_1$~$C_8$ alkyl or alkenyl (preferably, $C_1$~$C_4$ alkyl or alkenyl), unsubstituted phenyl or phenyl substituted by linear or branched $C_1$~$C_6$ alkyl (preferably, $C_1$~$C_4$ alkyl) or halogen; $R_{50}$ is selected from hydrogen, monovalent metal, linear or branched $C_1$~$C_8$ alkyl or alkenyl (preferably, $C_1$~$C_4$ alkyl or alkenyl), unsubstituted phenyl or phenyl substituted with one or more linear or branched $C_1$~$C_6$ alkyl (preferably, $C_1$~$C_4$ alkyl) or halogen.

Optimally, the compound of formula (1) or formula (2) is as follows:

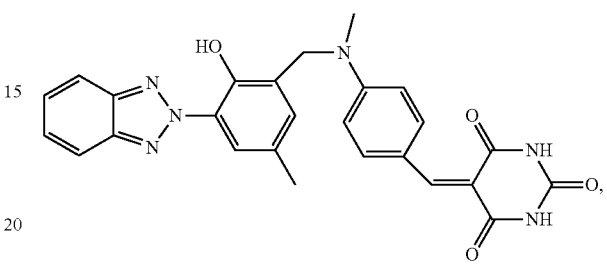

(7)

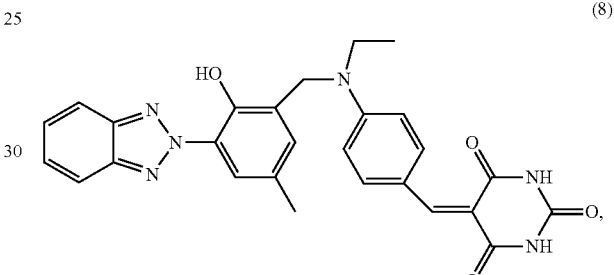

(8)

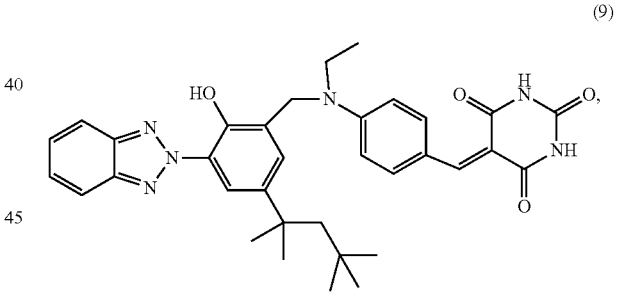

(9)

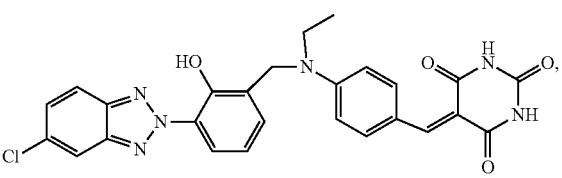

(12)

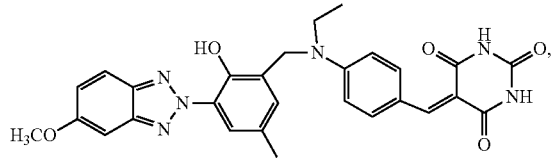

(14)

(16)
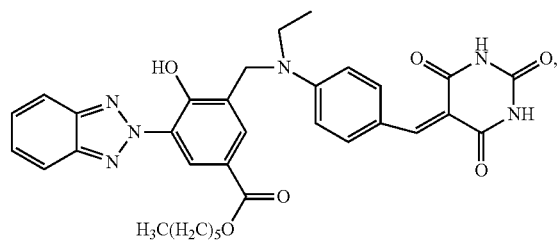
(18)
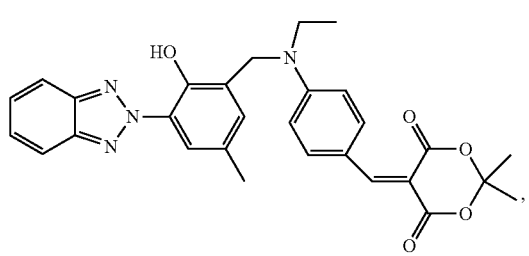
(19)
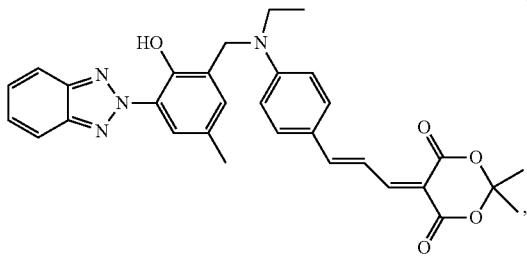
(22)
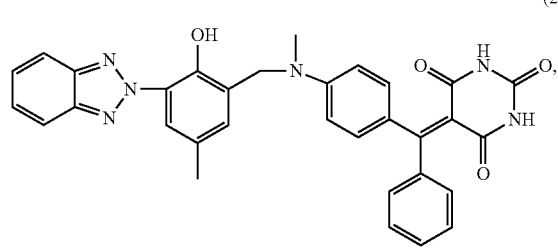
(25)
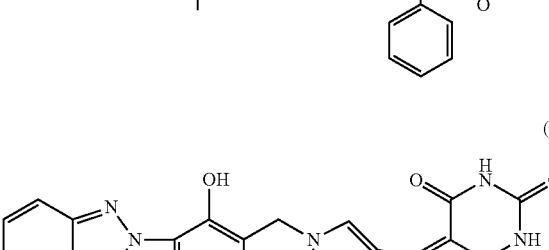
(27)
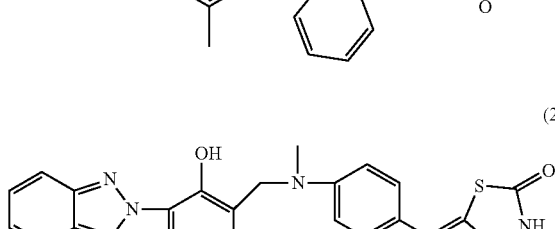
(29)
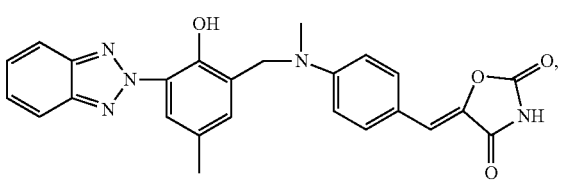
(30)
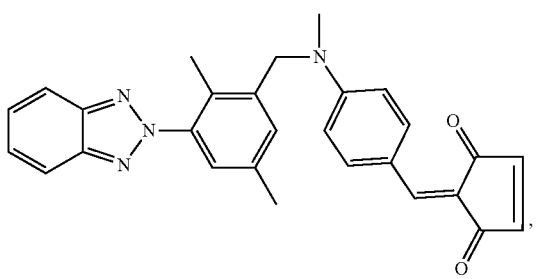
(32)
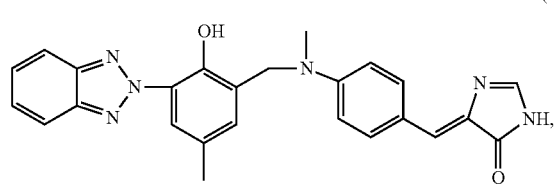
(33)
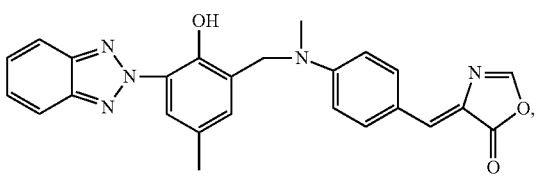
(34)
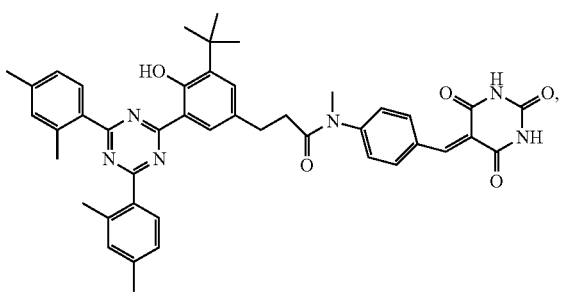
(38)
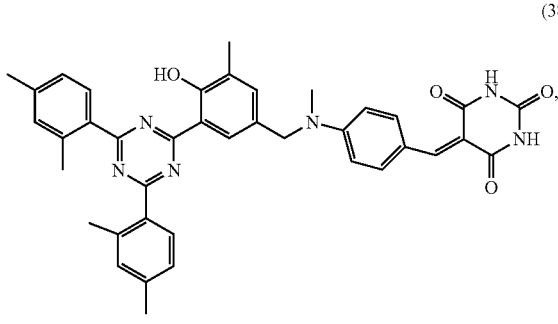

-continued
(40)
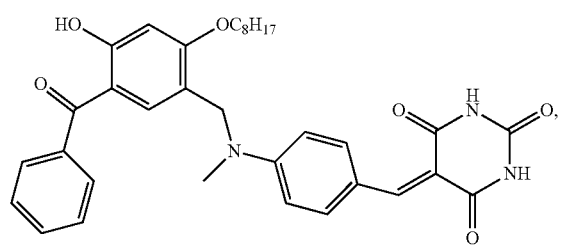
(42)
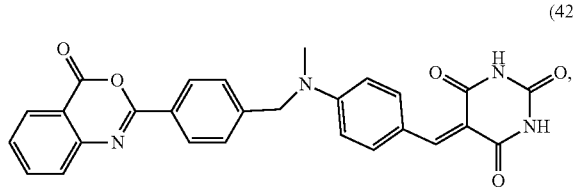
(47)
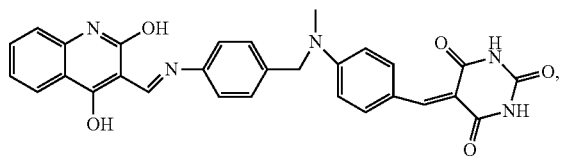
(49)
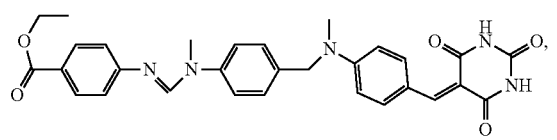
(51)
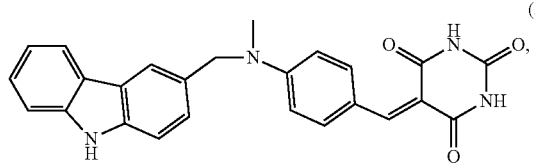
(53)
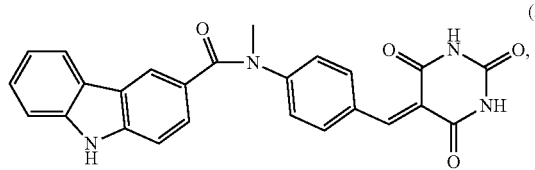
(55)
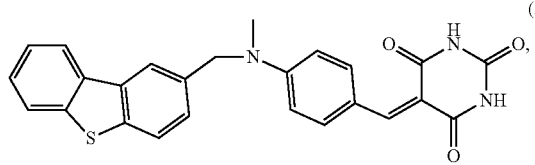
(57)
(60)
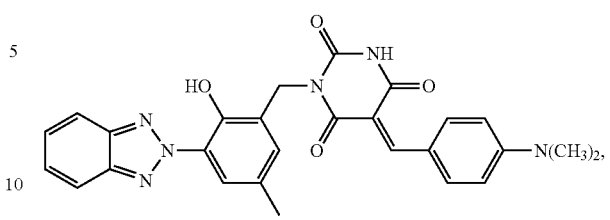
(62)
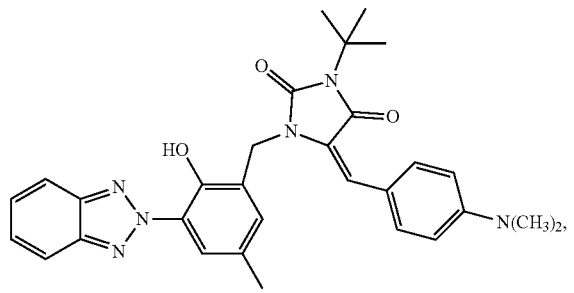
(67)
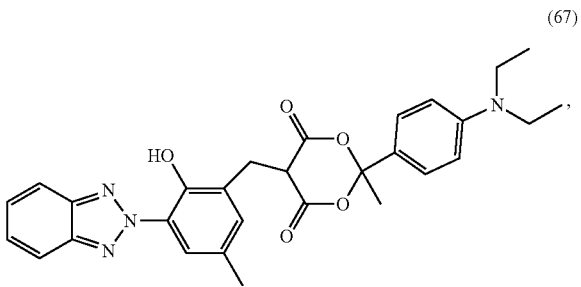
(71)
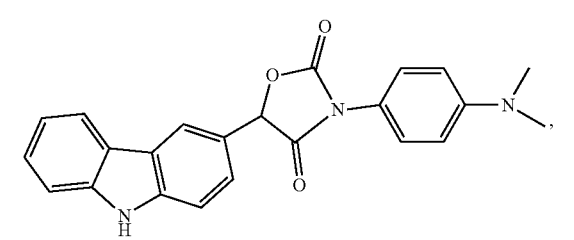
(76)
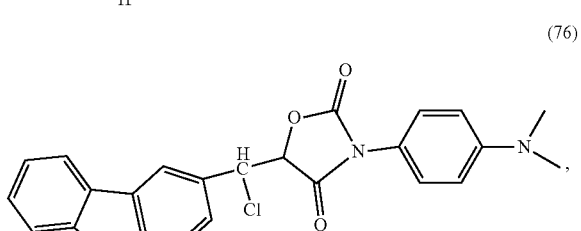
(81)
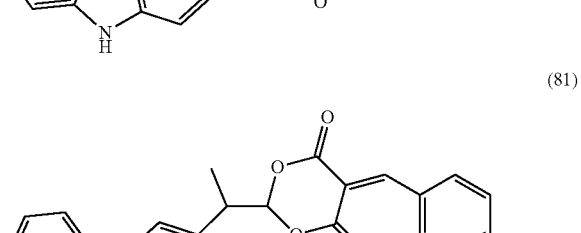

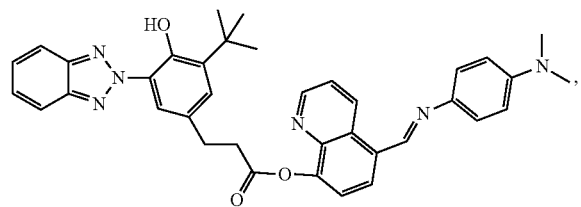

(84)

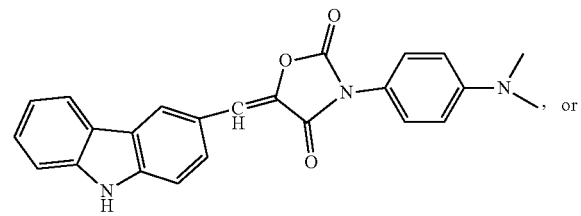

(88)

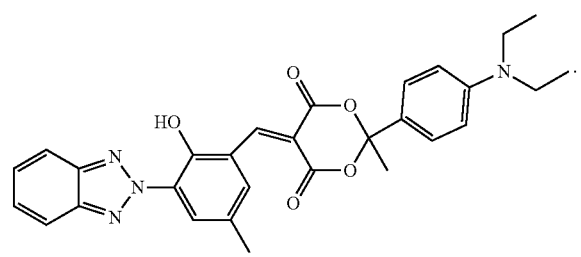

(90)

The method for preparing the compound of formula (1) or formula (2) is characterized by including one of the following reaction steps. The preparation of the compound of formula (1) includes one of the following reaction steps:

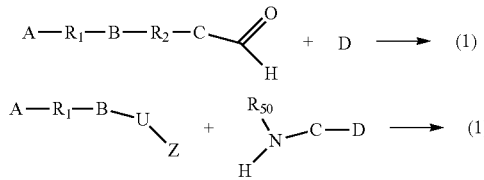

The preparation of the compound of formula (2) includes one of the following reaction steps:

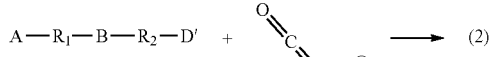

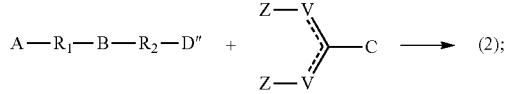

A to D ring, $R_1$ to $R_3$, are defined as above;

D' is the precursor of D ring, selected from

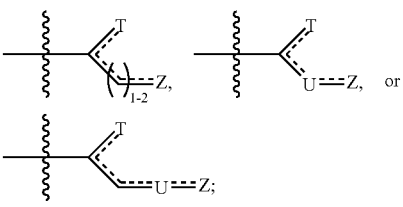

D" is the precursor of D ring,

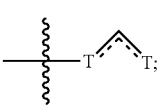

Z is a leaving group, including but not limited to halogen, $C_1$~$C_{10}$ sulfonate group, $C_1$~$C_{10}$ alkoxy; preferably, Z is selected from halogen, p-toluenesulfonate (OTs), mesylate (OMs), $C_1$~$C_4$ alkoxy. Preferably, the halogen is chlorine.

U and V are selected from C=O, C=S, C=N—$R_{51}$, C($R_{52}$)($R_{53}$); $R_{50}$~$R_{53}$ are the same or different and independently selected from a bond, hydrogen, linear or branched $C_1$~$C_8$ alkyl group, preferably, the alkyl group is a linear or branched $C_1$~$C_4$ alkyl group.

T is the same or different, and each is independently selected from NH, NH2, OH, or SH.

A specific preparation method of the compound (1) of the present invention includes the preparation methods of examples 1~11, 15~22, and 33. The preparation method of examples 1~4 compound is as follows:

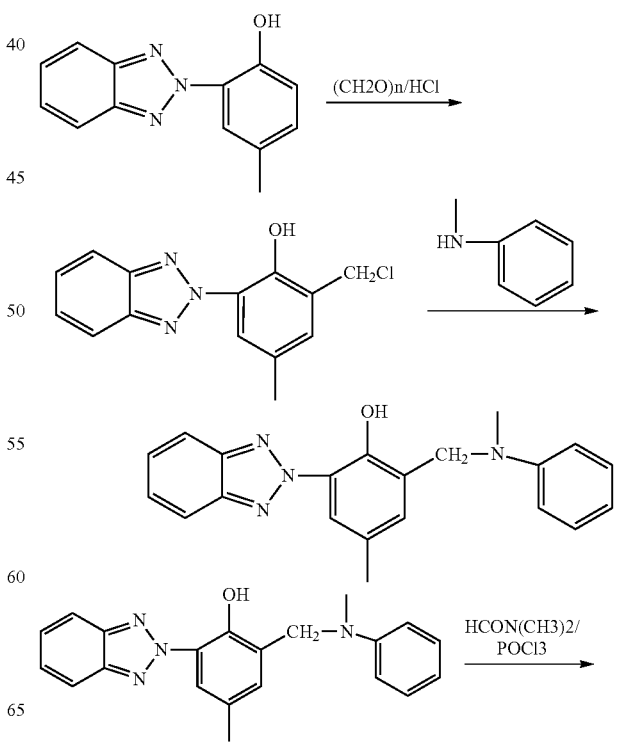

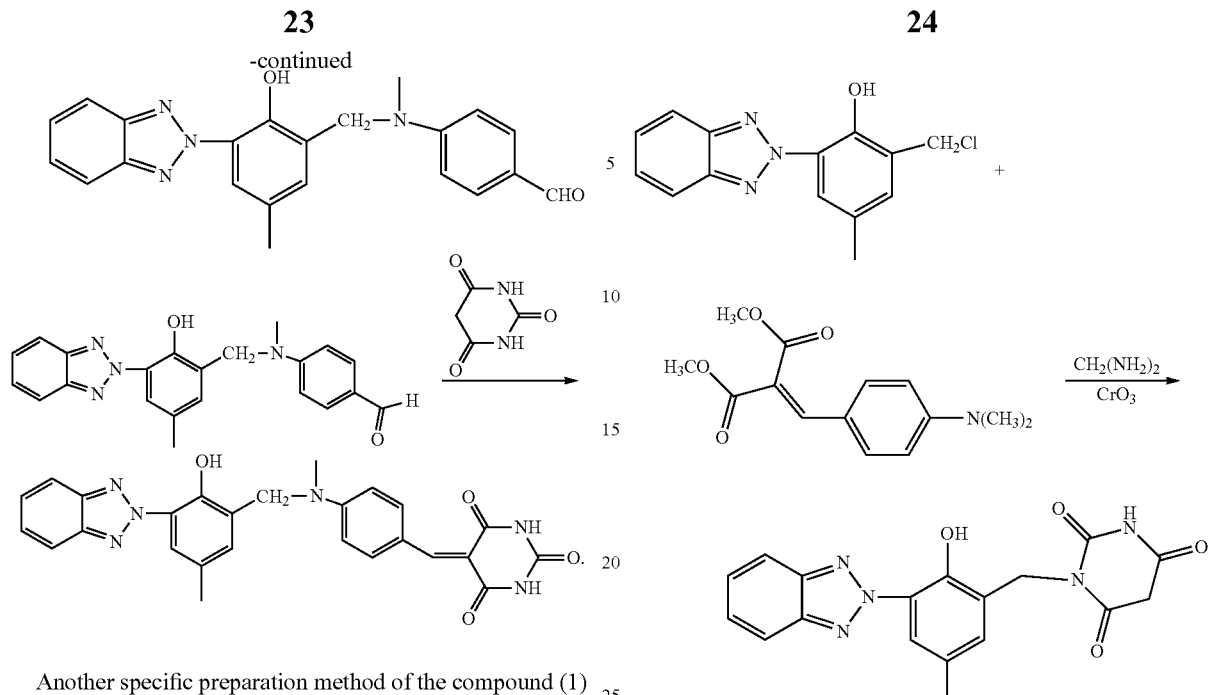

Another specific preparation method of the compound (1) for the present invention includes the preparation methods of examples 12~14 and 23~32. Wherein the preparation method of example 13 is as follows:

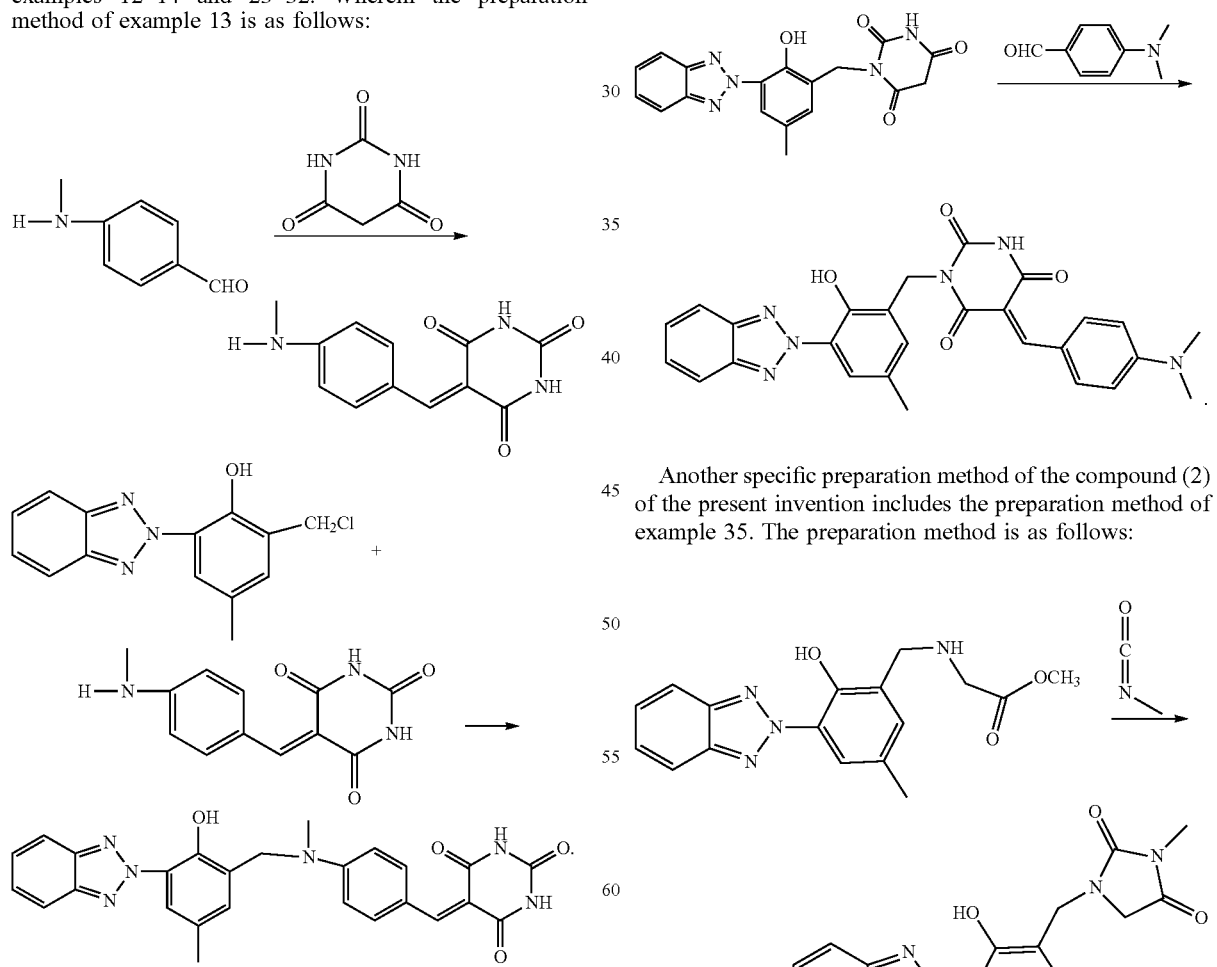

One of the specific preparation method of the compound (2) of the present invention includes the preparation method of example 34. The preparation method is as follows:

Another specific preparation method of the compound (2) of the present invention includes the preparation method of example 35. The preparation method is as follows:

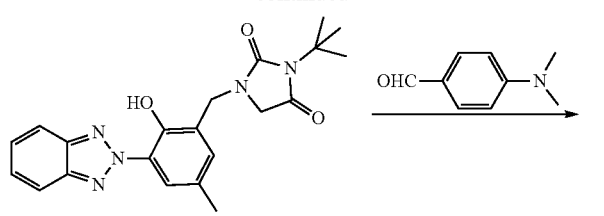

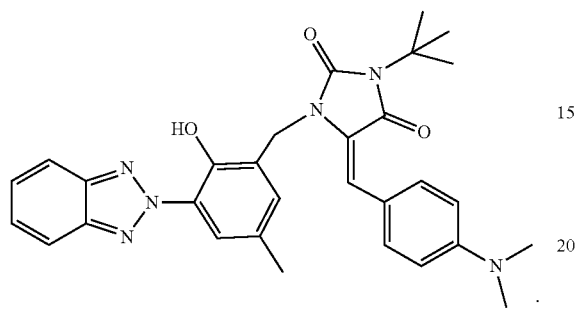

The third the specific preparation method of the compound (2) of the present invention includes the preparation method of example 36. The preparation method is as follows:

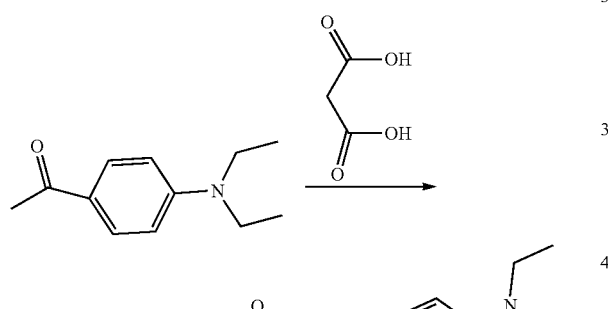

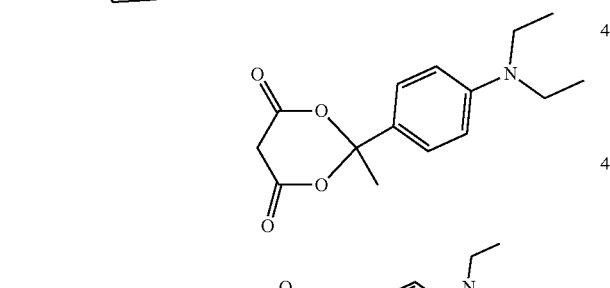

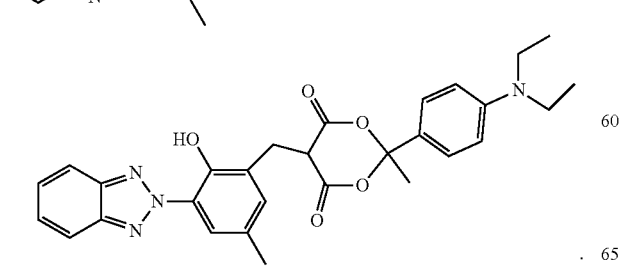

The forth of the specific preparation method of the compound (2) of the present invention includes the preparation method of example 37. The preparation method is as follows:

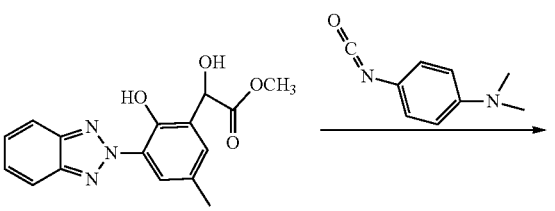

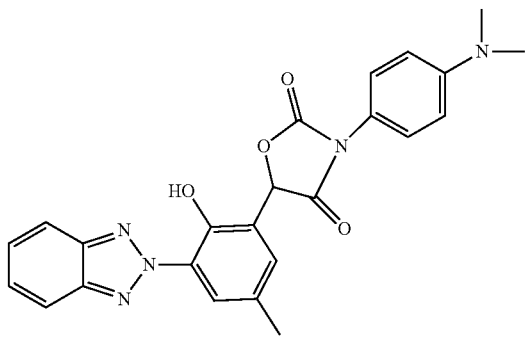

The fifth of the specific preparation method of the compound (2) of the present invention includes the preparation method of example 38. The preparation method is as follows:

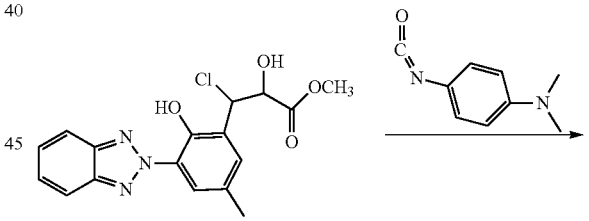

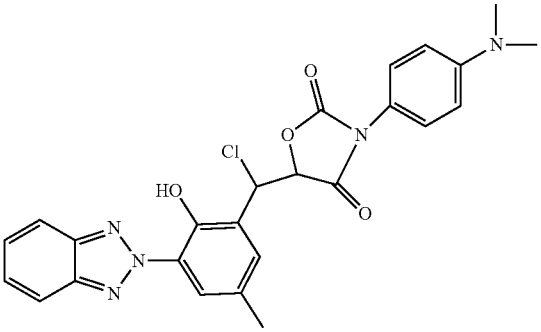

The sixth of the specific preparation method of the compound (2) of the present invention includes the preparation method of example 39. The preparation method is as follows:

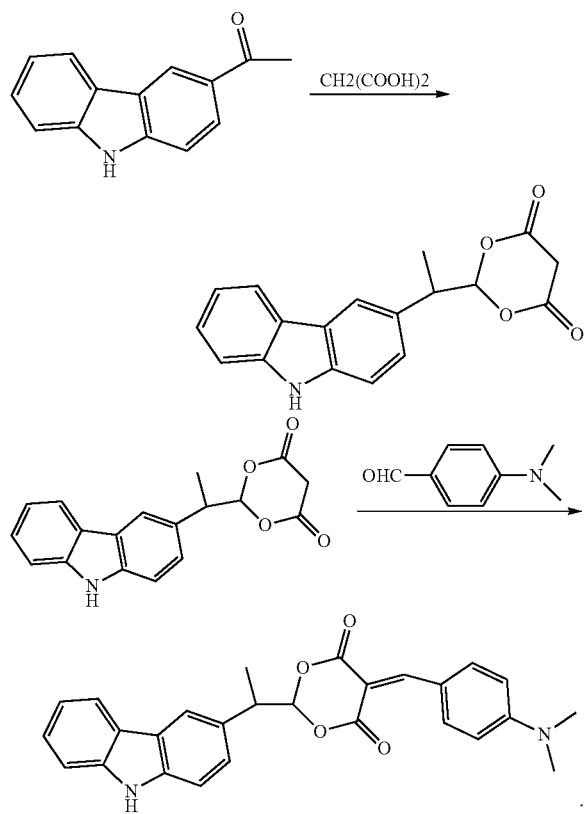

The traditional preparation method of benzotriazole compounds usually starts with 2-nitroaniline and various substituted phenols. The first step is to form an azo compound, and the second step is a reduction reaction to form a benzotriazole compound (U.S. Pat. No. 3,773,751), similar to example 6. The preparation method is as follows:

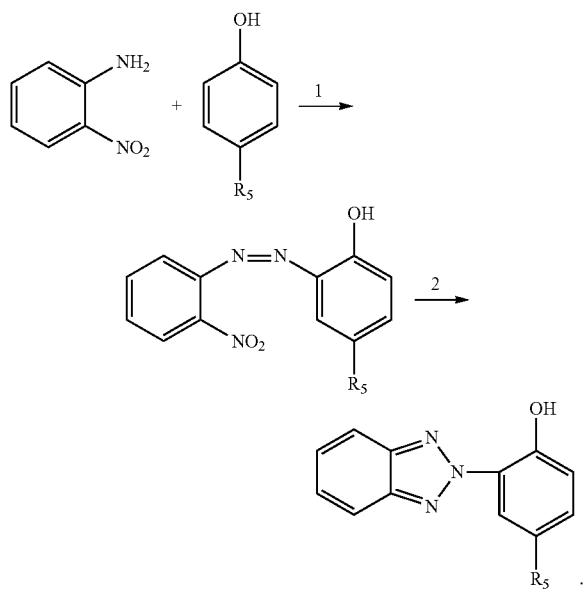

The compounds of the present invention can be applied to films. For example, it is used as a light conversion agent in agricultural film. It can also be used in anti-ultraviolet film or blue light film to protect eyes, other tissues or organic material. The compound of the present invention can be applied to general thin films or organic materials to protect the films or organic materials themselves. As another example, the compound of the present invention can be applied to the recording layer of an optical recording medium. The compounds of the present invention can also be used in combination with other compounds for other uses and the implementation of these applications can use general methods in industry.

Agricultural films are usually made of polyvinyl chloride, ethylene or low density polyethylene (LDPE), ethylene-vinyl acetate copolymer (EVA), metallocene linear polyethylene (MLLDPE) and other resins. After adding additives, it is made by blow molding and calendering process. Specific manufacturing methods, for example, take 1 kg of low-density polyethylene as the base material, 200 g of metallocene linear polyethylene, 5 g of light conversion agent, 8 g of antioxidant, 5 g of ultraviolet absorber, and 9 g of glyceride. After mixing, pass through a film blowing unit, according to conventional blow molding method. A transparent film usually has a thickness of 0.03~2.0 mm. The added amount of the light conversion agent depends on the type of crop and the thickness of the agricultural film needed, and the usual range includes but is not limited to 0.001% to 20%, preferably 0.2% to 5%.

In the manufacture of anti-ultraviolet film or anti-blue film, or agricultural film, the light conversion or anti-blue composition can also be coated on the base layer or release layer, and used after hardening. Or adopt a transfer coating process, which is first coated on the release film and then transferred to the base layer. A layer of release film is attached to the upper and lower layers of the film and is OCA (Optically Clear Adhesive). Coating methods are known techniques, including traditional brush coating, spray coating, curtain coating, roll coating, slit coating, air knife coating, knife coating, and metering bar coating. Drying methods include natural drying, microwave drying, ultraviolet drying, infrared drying, and hot air drying. The base layer includes one or a mixture of polyester, glass, polyethylene, polypropylene, polycarbonate, polyamide, polyacrylate, polymethacrylate, polyvinyl acetate, and polyvinyl chloride. The release film includes silicon-oxygen compound and non-silicon-oxygen compound materials. Light conversion or anti-blue light composition includes light conversion agent, anti-ultraviolet light agent, or anti-blue light agent, polymer, solvent, and/or auxiliary agent, and/or initiator, and/or monomer.

The compound of the present invention can be used in the recording layer of an optical recording medium. The spin coating method can be used to coat the organic dye recording layer on the substrate. The substrate can be made of polycarbonate (PC) or polyacrylamide. The thickness of the recording layer is usually several nanometers to tens of nanometers. After coating, a reflective layer is formed on the recording layer by sputtering. An adhesive layer is spin-coated, and a cover plate is adhered to the reflective layer through the adhesive layer to form an optical disc.

DETAILED DESCRIPTION

Figure 1:
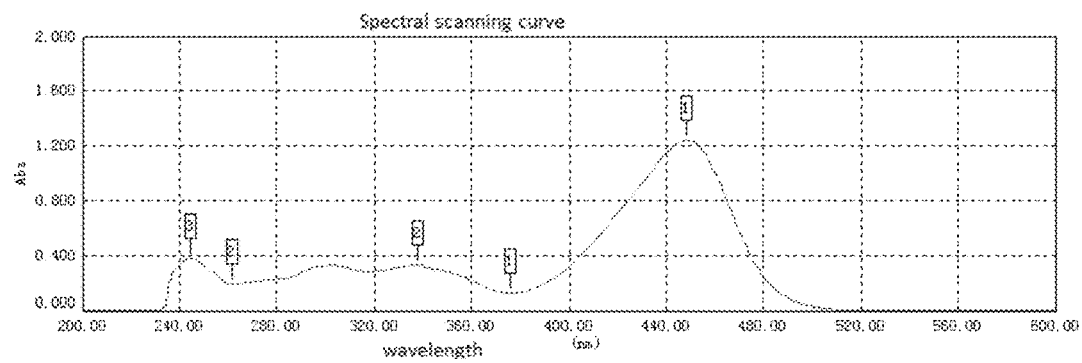
FIG. 1, UV-VIS absorption compound (7) of the present invention (10 mg/tetrahydrofuran)

Specific embodiments of the present invention will be described below, but the present invention is not limited to these embodiments.

A-R₁—B—R₂—C—R₃-D    (1)

TABLE 1

| Ex | A—R₁—B | R2 | C | R3 | D | R4 |
|---|---|---|---|---|---|---|
| 4 | 2-(2H-benzotriazol-2-yl)-4-methylphenol (HO on phenyl) | CH2NCH3 | benzene ring | —CH= | barbituric acid (methylene) | H, CH3, OH |
| 5 | 2-(2H-benzotriazol-2-yl)-4-methylphenol | CH2NC2H5 | benzene ring | —CH= | barbituric acid (methylene) | H, CH3, OH |
| 6 | 2-(2H-benzotriazol-2-yl)-4-(1,1,3,3-tetramethylbutyl)phenol | CH2NC2H5 | benzene ring | —CH= | barbituric acid (methylene) | H, CH, OH, C(CH3)2CH2C(CH3)3 |
| 7 | 5-chloro-2-(2H-benzotriazol-2-yl)phenol | CH2NC2H5 | benzene ring | —CH= | barbituric acid (methylene) | H, CH3, OH, Cl |
| 8 | 5-methoxy-2-(2H-benzotriazol-2-yl)-4-methylphenol | CH2NC2H5 | benzene ring | —CH= | barbituric acid (methylene) | H, CH3, OH, OCH3 |
| 9 | 3-(2H-benzotriazol-2-yl)-4-hydroxybenzoic acid hexyl ester | CH2NC2H5 | benzene ring | —CH= | barbituric acid (methylene) | H, CH3, OH, COO(CH2)5CH3 |
| 10 | 2-(2H-benzotriazol-2-yl)-4-methylphenol | CH2NC2H5 | benzene ring | —CH= | 2,2-dimethyl-1,3-dioxane-4,6-dione (methylene) | H, CH3, OH |
| 11 | 2-(2H-benzotriazol-2-yl)-4-methylphenol | CH2NC2H5 | benzene ring | —HC=CH—CH= | 2,2-dimethyl-1,3-dioxane-4,6-dione (methylene) | H, CH3, OH |

TABLE 1-continued the compounds of formula (1)

| Ex | A—R₁—B | R2 | C | R3 | D | R4 |
|---|---|---|---|---|---|---|
| 13 | benzotriazole-phenol-methyl with HO | CH2NCH3 | benzene | —CH= | barbiturate (pyrimidine-2,4,6-trione) | H, CH3, OH |
| 14 | benzotriazole-phenol-methyl with HO | CH2NCH3 | benzene | =C(Ph)— | barbiturate (pyrimidine-2,4,6-trione) | H, CH3, OH |
| 15 | benzotriazole-phenol-methyl with HO | CH2 | indole | —CH= | barbiturate (pyrimidine-2,4,6-trione) | H, CH3, OH |
| 16 | benzotriazole-phenol-methyl with HO | CH2NCH3 | benzene | —CH= | thiazolidine-2-one-4-thione | H, CH3, OH |
| 17 | benzotriazole-phenol-methyl with HO | CH2NCH3 | naphthalene | —CH= | barbiturate (pyrimidine-2,4,6-trione) | H, CH3, OH |
| 18 | benzotriazole-phenol-methyl with HO | CH2NCH3 | benzene | —CH= | oxazolidine-2,4-dione | H, CH3, OH |
| 19 | benzotriazole-phenol-methyl with HO | CH2NCH3 | benzene | —CH= | cyclopentene-1,3-dione | H, CH3, OH |
| 20 | benzotriazole-phenol-methyl with HO | CH2NCH3 | benzene | —CH= | indane-1,3-dione | H, CH3, OH |

TABLE 1-continued the compounds of formula (1)

| Ex | A—R₁—B | R2 | C | R3 | D | R4 |
|---|---|---|---|---|---|---|
| 21 | 2-(2H-benzotriazol-2-yl)-4-methylphenol | CH2NCH3 | phenyl | —CH= | 5-methylene-4H-imidazol-4-one | H, CH3, OH |
| 22 | 2-(2H-benzotriazol-2-yl)-4-methylphenol | CH2NCH3 | phenyl | —CH= | 5-methylene-1,3-oxazol-4(5H)-one | H, CH3, OH |
| 23 | 2-(4,6-diphenyl-1,3,5-triazin-2-yl)-6-tert-butylphenol | CH2CH2CONCH3 | phenyl | —CH= | 5-methylenebarbituric acid | H, CH3, OH, C(CH3)3, Ph |
| 24 | 2-(4,6-diphenyl-1,3,5-triazin-2-yl)-6-methylphenol | CH2NCH3 | phenyl | —CH= | 5-methylenebarbituric acid | H, CH3, OH, Ph |
| 25 | 2-hydroxy-4-octyloxybenzophenone | CH2NCH3 | phenyl | —CH= | 5-methylenebarbituric acid | H, OH, OC8H17 |
| 26 | 2-phenyl-4H-benzo[d][1,3]oxazin-4-one | CH2NCH3 | phenyl | —CH= | 5-methylenebarbituric acid | H |
| 27 | 3-((phenylimino)methyl)quinoline-2,4-diol | CH2NCH3 | phenyl | —CH= | 5-methylenebarbituric acid | H, OH |
| 28 | ethyl 4-((methyl(phenyl)amino)methyleneamino)benzoate | CH2NCH3 | phenyl | —CH= | 5-methylenebarbituric acid | H, CH3, COOC2H5 |

TABLE 1-continued the compounds of formula (1)

| Ex | A—R₁—B | R2 | C | R3 | D | R4 |
|---|---|---|---|---|---|---|
| 29 | (2-ethylphenyl)-NH-C(O)-C(O)-NH-(2-ethoxyphenyl) | CH2NCH3 | benzene ring | —CH= | barbituric acid (methylidene) | H, C2H5, OC2H5 |
| 30 | carbazole (9H-carbazole) | CH2NCH3 | benzene ring | —CH= | barbituric acid (methylidene) | H |
| 31 | carbazole (9H-carbazole) | CONCH3 | benzene ring | —CH= | barbituric acid (methylidene) | H |
| 32 | dibenzothiophene | CH2NCH3 | benzene ring | —CH= | barbituric acid (methylidene) | H |
| 33 | 3,5-di-tert-butyl-4-hydroxybenzoic acid 2,4-di-tert-butylphenyl ester | CH2NCH3 | benzene ring | —CH= | barbituric acid (methylidene) | C(CH3)3, H, OH |

A-R₁—B—R₂-D-R₃—C     (2)

TABLE 2 compounds of formula (2)

| example | A—R₁—B | R2 | D | R3 | C | R4 |
|---|---|---|---|---|---|---|
| 34 | 2-(2H-benzotriazol-2-yl)-4-methylphenol | CH2 | barbituric acid (N-linked, methylidene) | —CH= | benzene ring | N(CH3)2 |
| 35 | 2-(2H-benzotriazol-2-yl)-4-methylphenol | CH2 | 1,3-diisopropyl-hydantoin (methylidene) | —CH= | benzene ring | N(CH3)2, CH3, C(CH3)3 |

TABLE 2-continued compounds of formula (2)

| example | A—R₁—B | R2 | D | R3 | C | R4 |
|---|---|---|---|---|---|---|
| 36 | 2-(2H-benzotriazol-2-yl)-4-methylphenol | CH2 | 1,3-dioxane-4,6-dione (Meldrum-type, 5,5-disubst.) | A bond | phenyl | H, N(CH3)2, CH3, |
| 36 | 2-(2H-benzotriazol-2-yl)-4-methylphenol | CH= | 1,3-dioxane-4,6-dione (5-ylidene) | A bond | phenyl | H, N(CH3)2, CH3, |
| 37 | carbazole | A bond | oxazolidine-2,4-dione (N,5-disubst.) | A bond | phenyl | H, N(CH3)2, C2H5, |
| 38 | carbazole | CHCl | oxazolidine-2,4-dione (N,5-disubst.) | A bond | phenyl | H, N(C2H5)2, C2H5, |
| 38 | carbazole | CH= | oxazolidine-2,4-dione (5-ylidene) | A bond | phenyl | H, N(C2H5)2, C2H5, |
| 39 | carbazole | CHCH3 | 1,3-dioxane-4,6-dione (5-ylidene) | —CH= | phenyl | H, N(CH3)2 |
| 40 | 2-(2H-benzotriazol-2-yl)-6-tert-butylphenol | CH2CH2COO | quinoline (5,7-disubst.) | —C=N— | phenyl | H, OH, N(CH3)2, C(CH3)3 |

Example 1

2-(2-hydroxy-3-(chloromethyl)-5-methyl)benzotriazole (compound 3)

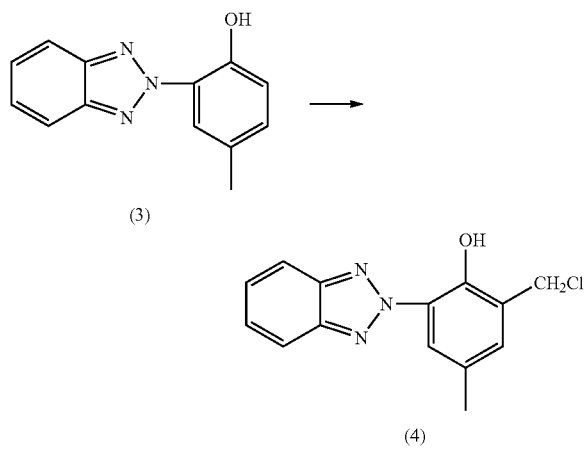

Add 350 g of 2-(2-hydroxy-5-methyl)benzotriazole (UV-P, compound 3), 55 g of paraformaldehyde, 2000 g of acetic acid, and 300 g of 35% hydrochloric acid to a 5000 ml reaction flask, and heat to 60° C. The reaction was kept for 10 hours, and samples were taken to monitor the reaction. By cooling, washing with water, and drying, the white powder (chloromethyl UV-P, compound 4) was obtained with a yield of 96%. $C_{14}H_{12}ClN_3O$, mp: 163~164° C.

Example 2

2-(2-hydroxy-3-(N,N-dimethylaniline)-5-methyl)benzotriazole (compound 5)

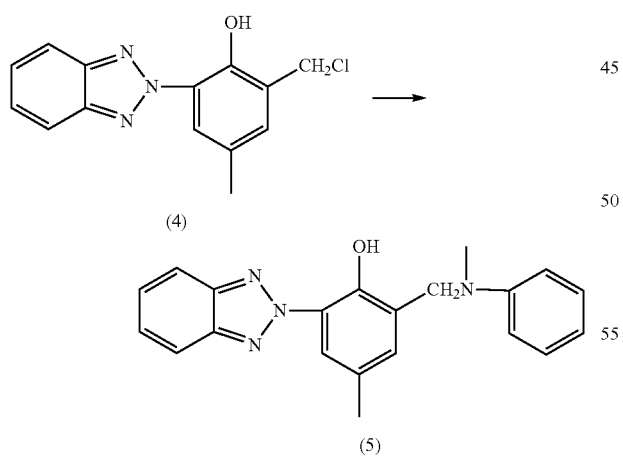

180 ml of toluene, 17 g of potassium carbonate, 13.9 g of N-methylaniline, 0.2 g of phase catalyst, and 33.3 g of compound (4) were put together. The temperature was raised to 90~100° C. for 5 hours, and samples were taken to monitor the reaction. Cool down to 30° C. and wash with water. Add 180 g of methanol, stir, filter, and dry to obtain a solid (compound 5). The purity is 98.3%, and the yield is 84%. $C_{21}H_{20}N_4O$, mp: 98~100° C.

Example 3

2-(2-hydroxy-3-(4-formyl-N,N-dimethylaminobenzene)-5-methyl)benzotriazole (compound 6)

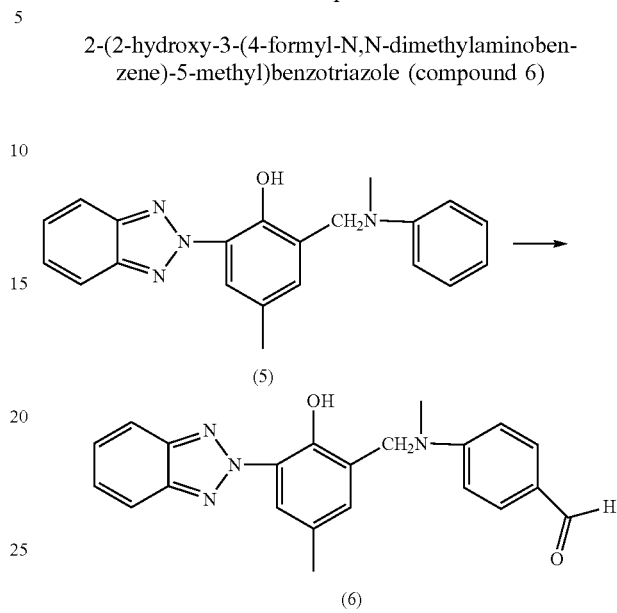

Mix 35 g of compound (5), 8.7 g of DMF, and add 18.4 g of phosphorus oxychloride dropwise at 20~25° C. for about 2 hours. The temperature was raised to 90° C. to react for 2 hours, and samples were taken to monitor the reaction (Vilsmeier-Haack formylation). The product was slowly added to 300 g of water below 30° C. for hydrolysis, After the addition, it was neutralized with 30% liquid caustic so as to adjust the pH to 8, and the solid is filtered. Dissolve the solid with toluene, and washed with water, then cooled to 15° C. The solid was separated, and dried to obtain 31.8 g of yellow solids (compound 6). $C_{21}H_{19}N_4O_2$, mp: 111~113° C.

Example 4

5-(4-((3-(2H-benzo[d][1,2,3]triazol-2-yl)-2-hydroxy-5-methylbenzyl) (methyl)amino)ylidenebenzyl)pyrimidine-2,4,6 (1H,3H,5H) trione (compound 7)

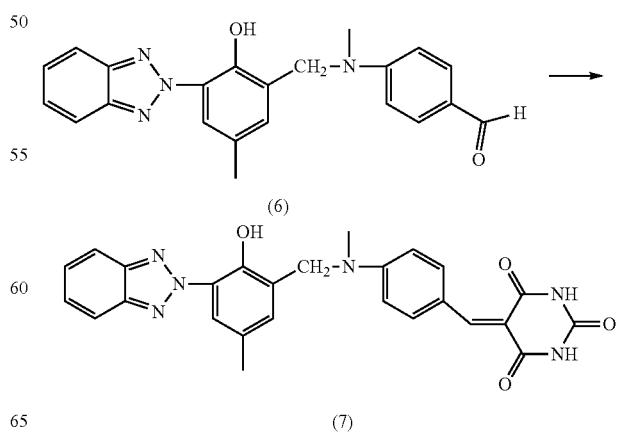

50 g of compound (6) and 17.1 g of barbituric acid were dissolved in toluene, and 5 g of ammonium acetate and 10 g of acetic acid were added and kept at 80~90° C. for 1 hour. Then the temperature was raised to reflux for 8 hours, and the reaction was monitored by sampling. After the reaction was completed, the temperature was lowered, and the solid was filtered, then washed with toluene, and dichloroethane. Then it was filtered, washed with water, and dried to obtain compound (7). Yield: about 80%. $C_{26}H_{22}N_6O_4$, mp: 262~270° C.

Example 5

5-(4-((3-(2H-benzo[d][1,2,3]triazol-2-yl)-2-hydroxy-5-methylbenzyl)(ethyl)amino)benzylidene)pyrimidine-2,4,6 (1H,3H,5H)-trione

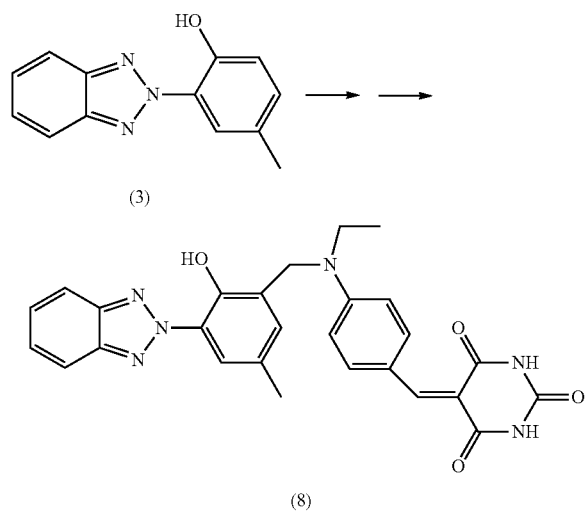

According to the method of examples 1~4, but using N-ethylaniline instead of N-methylaniline, compound (8) was obtained. $C_{27}H_{24}N_6O_4$, mp: 263~267° C.

Example 6

5-(4-((3-(2H-benzo[d][1,2,3]triazol-2-yl)-2-hydroxy-5-(2,4,4-trimethylpentan-2-yl)benzyl)(ethyl)amino)benzylidene)pyrimidine-2,4,6 (1H,3H,5H)-trione

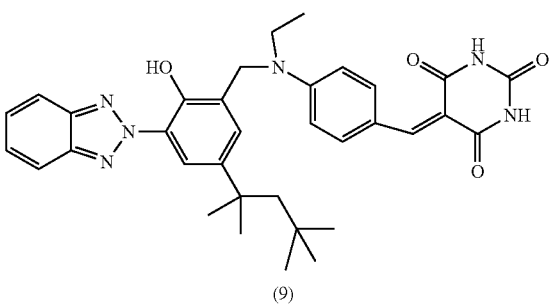

2-(2-hydroxy-5-tert-octylphenyl)-2H-benzotriazole (compound 10) is obtained from Eutec co. (Eusorb 329, melting point: 102~106° C.), or can be prepared as described below. 13.8 g of o-nitroaniline was added to 25 ml of 37% hydrochloric acid and stirred, diluted with 40 ml of water and cooled to −15° C. Add 7.5 g of sodium nitrite (dissolved in water) and keep the temperature at 0~5° C. to obtain the diazonium salt (Diazonium). Mix 5.2 g of 4-tert-Octylphenol, 20 ml of petroleum ether, 5 ml of water and 2.5 g of calcium hydroxide, and took samples to monitor the reaction. After the reaction was completed, 20 g of ice was added and the temperature was raised to 0° C. Add the aforementioned diazonium salt and stir for 2 hours. It was neutralized by adding concentrated hydrochloric acid and dried to obtain 2-((2-nitrophenyl)diazenyl)-4-(2,4,4-trimethylpent-2-yl) phenol (Compound 11). $C_{20}H_{25}N_3O_3$, mp: 114~115° C.

Dissolve 35.7 g of compound (11) in 100 ml of petroleum ether, add 17.2 g of zinc and 100 ml of water. 41.6 g of NaOH solution (25%) was added within 4 hours at 50° C. and left for 1 hour. 100 ml of concentrated hydrochloric acid was added and left for 2 hours, samples were taken to monitor the reaction, the organic layer was washed with water, and the solvent was removed to obtain compound (10). $C_{20}H_{25}N_3O$, mp: 102~106° C.

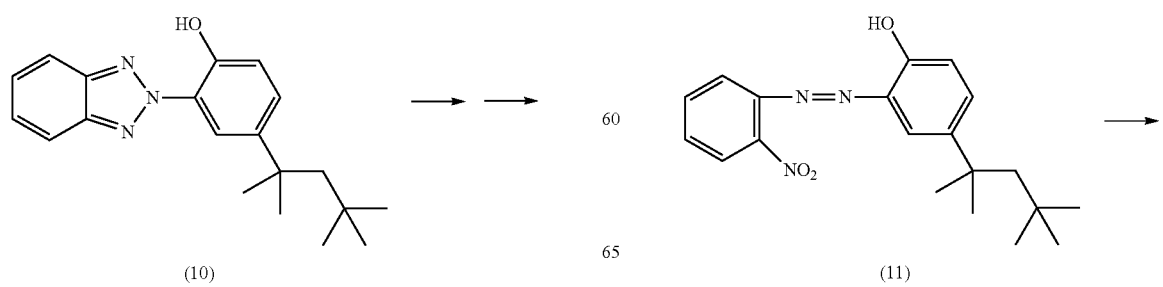

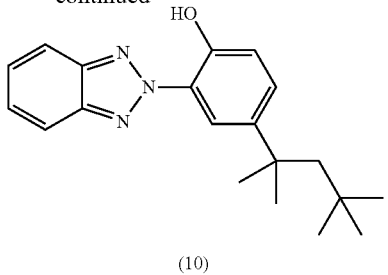

(10)

According to the method of example 1~5, but using 2-(2-hydroxy-5-tert-octylphenyl)-2H-benzotriazole (Eusorb 329, compound 10) instead of UV-P (compound 3) as a starting material, compound (9) was obtained. $C_{34}H_{38}N_6O_4$, m/z: 594.3 $[M]^+$.

Example 7

5-(4-((3-(5-chloro-2H-benzo[d][1,2,3]triazol-2-yl)-2-hydroxybenzyl)(ethyl)amino)benzylidene)pyrimidine-2,4,6 (1H,3H,5H)-trione

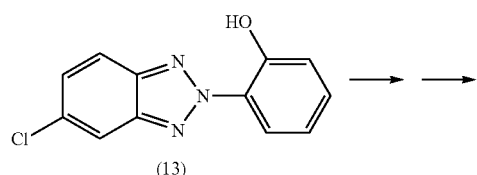

(13)

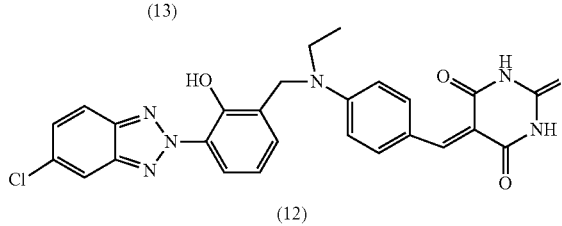

(12)

According to the method of example 6, but using 4-chloro-2-nitroaniline instead of o-nitroaniline as the starting material, 2-(2'-hydroxy-phenyl)-5-chloro-benzotriazole (compound 13) was obtained, $C_{12}H_8ClN_3O$, mp: 139~140° C. According to the method of example 1~5, but using 2-(2'-hydroxy-phenyl)-5-chloro-benzotriazole (compound 13) instead of UV-P (compound 3) as the starting material, the compound (12) was obtained. $C_{26}H_{21}ClN_6O_4$, m/z: 516.1 $[M]^+$.

Example 8

5-(4-(ethyl(2-hydroxy-3-(5-methoxy-2H-benzo[d][1,2,3]triazol-2-yl)-5-methylbenzyl)amino)benzylidene)pyrimidine-2,4,6 (1H,3H,5H)-trione

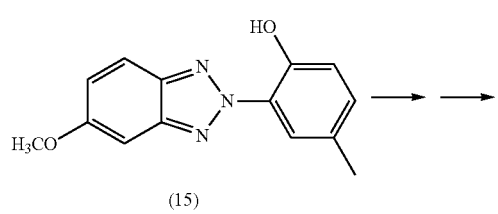

(15)

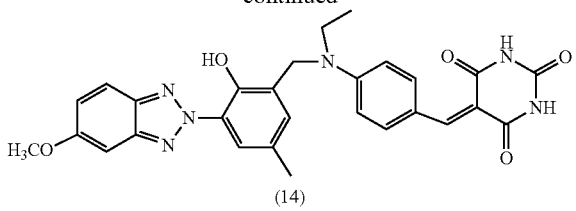

(14)

According to the method of example 6, but using 4-methoxy-2-nitroaniline instead of o-nitroaniline as the starting material, 2-(2'-hydroxy-phenyl)-5-chloro-benzotriazole (compound 15) was obtained. $C_{14}H_{13}N_3O_2$, mp: 126~27° C. According to the method of example 1~5, but using 2-(2'-hydroxy-phenyl)-5-methoxy-benzotriazole (Compound 15) instead of UV-P (Compound 3) as the starting material, compound (14) was obtained. $C_{28}H_{26}N_6O_5$, m/z: 526.2 $[M]^+$.

Example 9

3-(2H-benzo[d][1,2,3]triazol-2-yl)-5-((ethyl(4-((2,4,6-trioxotetrahydropyrimidine-5 (2H)-ylidene)methyl)phenyl)amino)methyl)-4-hydroxybenzoic acid methyl ester (compound 16)

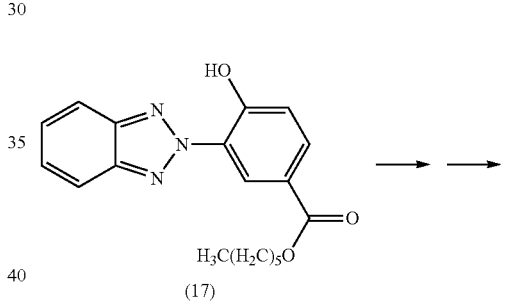

(17)

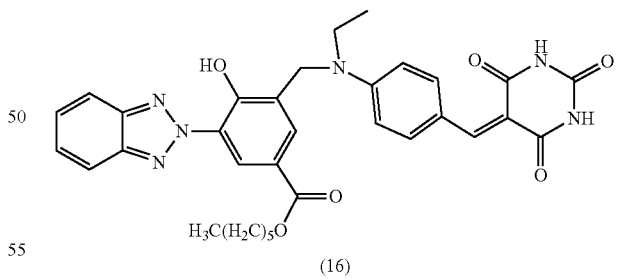

(16)

According to the method of example 6, but using 4-hydroxybenzoic acid to replace 4-p-tert-octylphenol, and 3-(2H-benzo[d][1,2,3]triazol-2-yl)-4 was obtained. Thionyl chloride was added, and the temperature was raised to reflux for 2 hours. The thionyl chloride was evaporated and n-hexanol was added to reflux, and the reaction was monitored by sampling. 3-(2H-benzo[d][1,2,3]triazol-2-yl)-4-hydroxybenzoic acid hexyl ester (Compound 17) was obtained. $C_{19}H_{21}N_3O_3$, mp: 83~84° C.

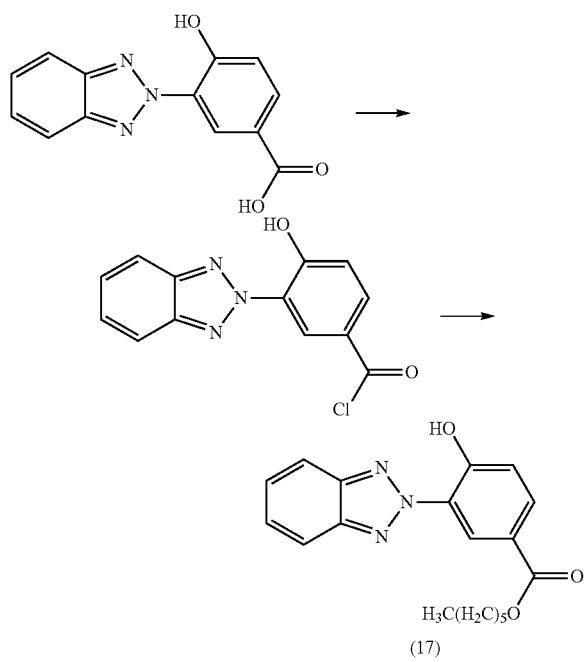

According to the method of example 1~5, but using 3-(2H-benzo[d][1,2,3]triazol-2-yl)-4-hydroxybenzoic acid hexyl ester (Compound 17) instead of UV-P (Compound 3) to obtain compound (16). $C_{33}H_{34}N_6O_6$, m/z: 610.3 $[M]^+$.

Example 10

5-(4-((3-(2H-benzo[d][1,2,3]triazol-2-yl)-2-hydroxy-5-methylbenzyl)(ethyl)amino)ylidenebenzyl)-2,2-Dimethyl-1,3-dioxane-4,6-dione (Compound 18)

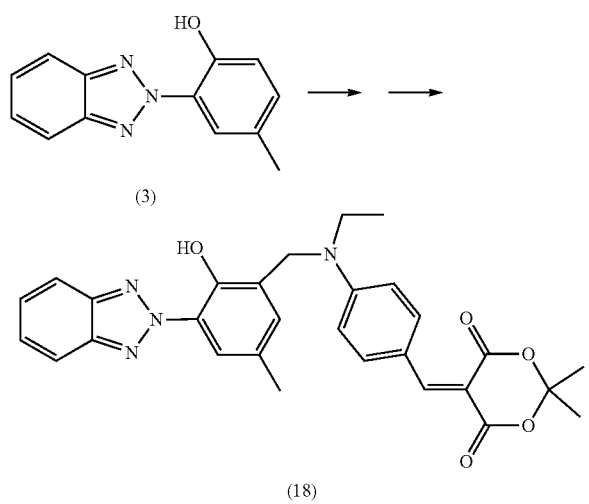

20 g of compound (6) and 8.2 g of Meldrum's acid were dissolved in toluene, and 4.1 g of ammonium acetate and 10 g of acetic acid were added. Reflux and dehydrate for 4 hours, samples were taken to monitor the reaction. After the reaction was completed, the solid was filtered, and dissolved with dichloroethane at elevated temperature, and then washed with water. Dichloroethane is distilled out, and toluene is added for recrystallization to obtain compound (18). $C_{29}H_{28}N_4O_5$, mp: 220~224° C.

Example 11

5-(4-((3-(2H-benzo[d][1,2,3]triazol-2-yl)-2-hydroxy-5-methylbenzyl)(ethyl)amino)ylidenebenzyl)-2,2-Dimethyl-1,3-dioxane-4,6-dione (Compound 19)

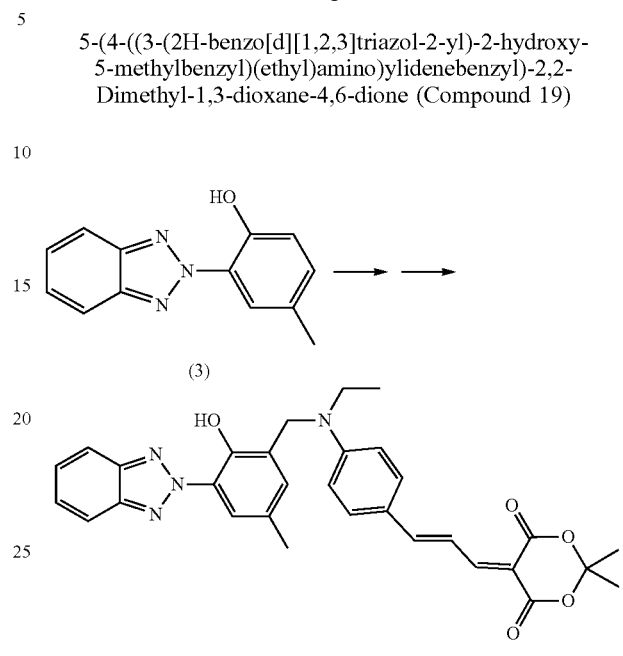

12 g of compound (6) was added to 200 ml of a solution of 1% sodium hydroxide and 15% ethanol, and 5 g of 30% acetaldehyde aqueous solution was added dropwise. After an overnight reacting, 15 g of NaCl was added and stirred, and the pH was adjusted to neutral with dilute hydrochloric acid. Then it was extracted with ethyl acetate and dried to obtain 3-(4-((3-(2H-benzo[d][1,2,3]triazol-2-yl)-2-hydroxy-5-methyl Benzyl) (ethyl)amino)phenyl) acrolein (20).

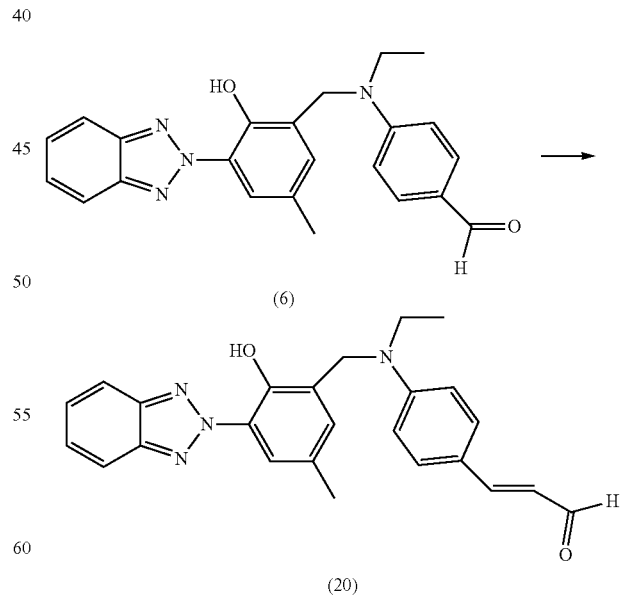

According to the method of example 10, the compound (20) was added to Mildren's acid, ammonium acetate and acetic acid to obtain the compound (19). $C_{31}H_{30}N_4O_5$, m/z: 538.2 $[M]^+$.

Example 12

5-(4-(methylamino)benzylidene)pyrimidine-2,4,6 (1H,3H,5H)-trione (Compound 21)

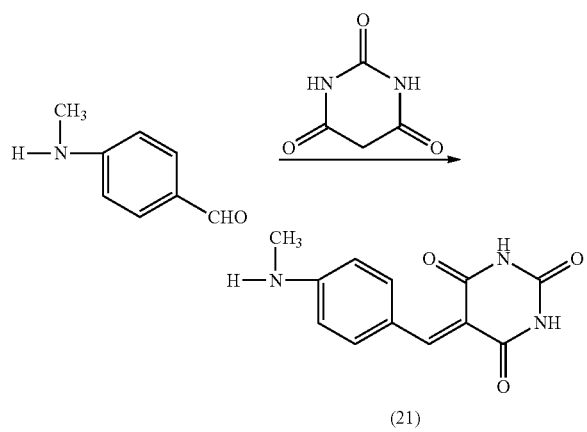

(21)

20 g of barbituric acid and 13.6 g of 4-methylaminobenzaldehyde were dissolved in dichloromethane. Add molecular sieve to remove water and install calcium chloride pipe for waterproof. 1 ml of piperidine and 0.6 ml of acetic acid were added, and heated to reflux for 2 hours. During the reaction, fresh molecular sieve was added, and samples were taken to monitor the reaction. After the completion of the reaction, the solvent was removed, and the compound (21) was obtained after pickling and drying. $C_{12}H_{11}N_3O_3$, m/z: 245.1 $[M]^+$.

Example 13

5-(4-((3-(2H-benzo[d][1,2,3]triazol-2-yl)-2-hydroxy-5-methylbenzyl)(methyl)amino)ylidenebenzyl)pyrimidine-2,4-,6 (1H,3H,5H) trione (compound 7)

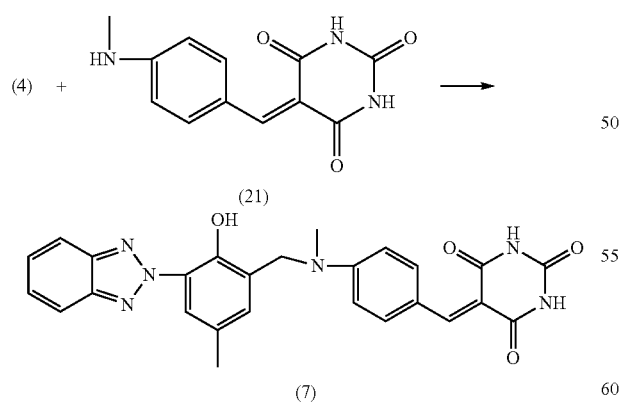

According to the method of example 2, but replace N-methylaniline with compound (21), and compound (7) was obtained. In the H1-NMR of the starting compound (4), the chemical shift of 4.6 disappeared (—CH$_2$Cl), and the chemical shift of 5.0 was appeared (compound 7, —CH$_2$N), indicating that the reaction was completed. The melting point range is the same as that of compound (7) prepared by the method of example 4.

Example 14

3-(4-((3-(2H-benzo[d][1,2,3]triazol-2-yl)-2-hydroxy-5-methylbenzyl)(methyl)amino)benzene Yl)-2-cyano-3-phenyl acrylate (compound 22)

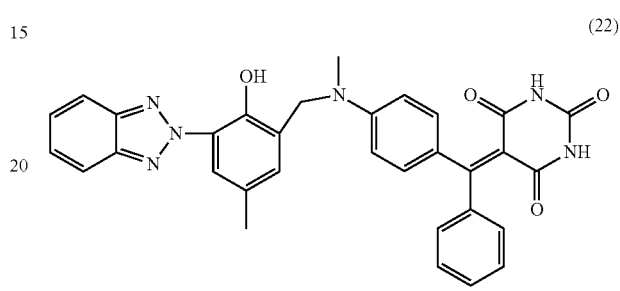

(22)

According to the method of example 2, but using 4-methylaminobenzophenone (compound 23) instead of compound N-methylaniline, compound (24) was obtained.

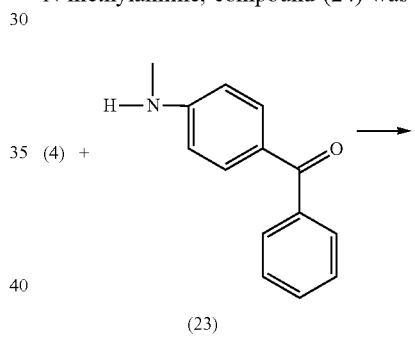

(23)

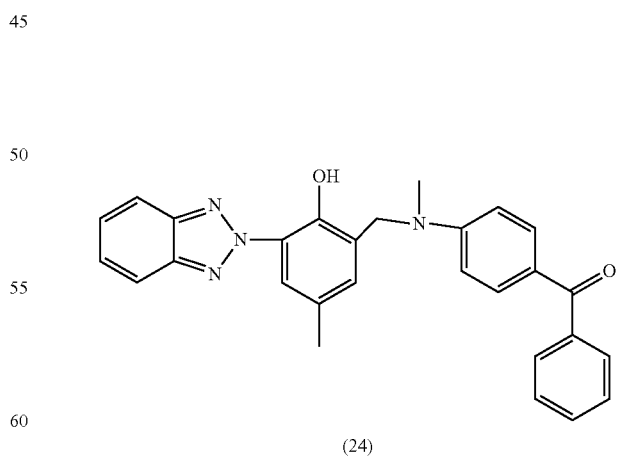

(24)

According to the method of example 4, compound (24) was used to replace compound (6). Column chromatography was used for isolation to obtain compound (22). $C_{32}H_{26}N_6O_4$, m/z: 558.2 $[M]^+$.

Example 15

5-((1-(3-(2H-benzo[d][1,2,3]triazol-2-yl)-2-hydroxy-5-methylbenzyl)-1H-indol-3-yl)methylene)pyrimidine-2,4,6-(1H,3H,5H)-trione (compound 25)

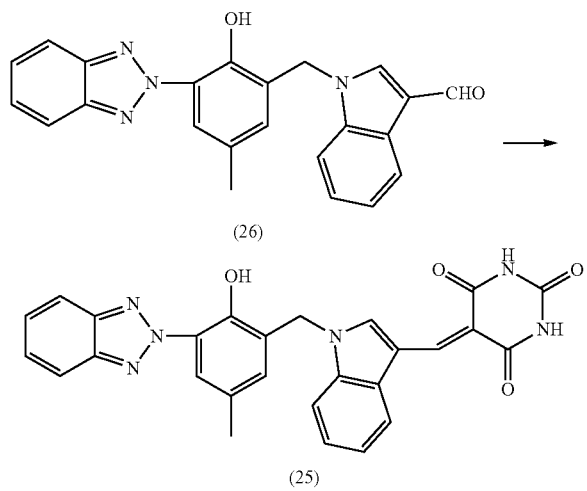

According to the method of example 2, 3-indolecarboxaldehyde was used, instead of N-methylaniline, and column chromatography was used to obtain compound (26). According to the method of example 3 and 4, compound (25) was used, instead of compound (6), and separated by column chromatography to obtain compound (25), $C_{27}H_{20}N_6O_4$. m/z: 492.2 [M]$^+$. 3-indole formaldehyde is common used for industry and can be prepared in the following way (Vilsmeier reaction): 16 g of POCl3 and 30 g of DMF were mixed under ice bath in 30 minutes, and 11 g of indole compound solution (DMF) was slowly added. The temperature was raised to 35° C. and stirred for 1 hour. Add 50 g of crushed ice to the obtained paste and stir, and add 0.1M NaOH slowly while stirring. After washing with water, recrystallize it with ethanol to obtain 3-indole formaldehyde. $C_9H_7NO$, mp: 196~197° C.

Example 16

5-(4-((3-(2H-benzo[d][1,2,3]triazol-2-yl)-2-hydroxy-5-methylbenzyl)(methyl)amino)ylidenebenzyl)-4-thiothiazol-2-one (compound 27)

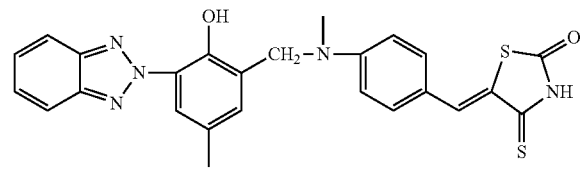

According to the method of example 4, the compound 4-thiothiazol-2-one (CAS RN. 4303-29-1) was used to replace the barbituric acid compound to obtain compound (27). $C_{25}H_{21}N_5O_4$, m/z: 455.2 [M]$^+$.

Example 17

5-(4-((3-(2H-benzo[d][1,2,3]triazol-2-yl)-2-hydroxy-5-methylbenzyl)(methyl)amino)ylidenebenzyl)-4-thiothiazol-2-one (Compound 27)

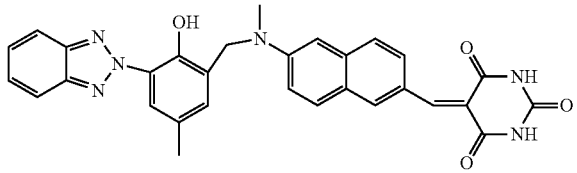

According to the method of example 15, 6-(methylamino)-2-naphthaldehyde was used, instead of 3-indole formaldehyde, to obtain compound (28). $C_{30}H_{24}N_6O_4$, m/z: 532.2 [M]$^+$.

Example 18

5-(4-((3-(2H-benzo[d][1,2,3]triazol-2-yl)-2-hydroxy-5-methylbenzyl)(methyl)amino)ylidenebenzyl) oxazolidine-2,4-dione (Compound 29)

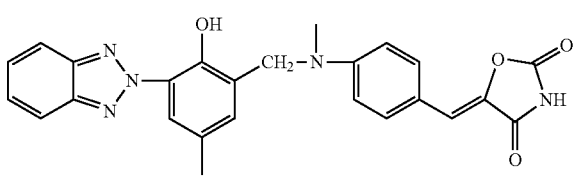

According to the method of example 4, the compound oxazolidine-2,4-dione (CAS RN. 2346-26-1) was used to replace the barbituric acid compound to obtain compound (29). $C_{25}H_{21}NO_4$, m/z: 455.2 [M]$^+$.

Example 19

2-(4-((3-(2H-benzo[d][1,2,3]triazol-2-yl)-2-hydroxy-5-methylbenzyl)(methyl)amino)ylidenebenzyl)cyclopent-4-ene-1,3-dione (compound 30)

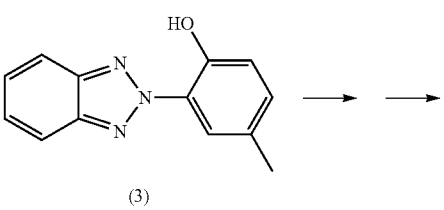

-continued

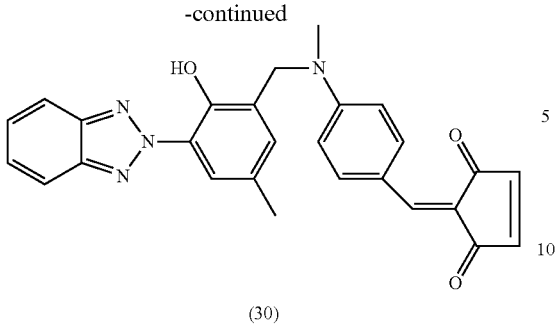

(30)

According to the method of example 4, 4-cyclopentene-1,3-dione compound was used to replace the barbituric acid compound to obtain compound (30). $C_{26}H_{19}N_4O_3$, m/z: 435.2 [M]$^+$.

Example 20

2-(4-((3-(2H-benzo[d][1,2,3]triazol-2-yl)-2-hydroxy-5-methylbenzyl)(methyl)amino)ylidenebenzyl)-1H-indene-1,3 (2H)-dione (Compound 31)

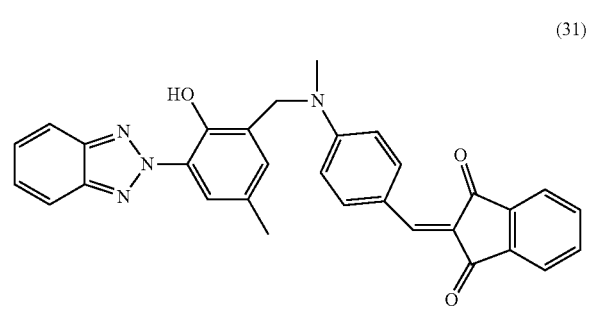 [SMILES: Cc1cc(CN(C)c2ccc(C=C3C(=O)c4ccccc4C3=O)cc2)c(O)c(-n2nc3ccccc3n2)c1]

(31)

According to the method of example 4, compound 1H-indene-1,3 (2H)-dione was used to replace the barbituric acid compound to obtain compound (31). $C_{31}H_{24}N_4O_3$, m/z: 500.2 [M]$^+$.

Example 21

5-(4-((3-(2H-benzo[d][1,2,3]triazol-2-yl)-2-hydroxy-5-methylbenzyl)(methyl)amino)ylidenebenzyl)-3,5-dihydro-4H-imidazol-4-one (Compound 32)

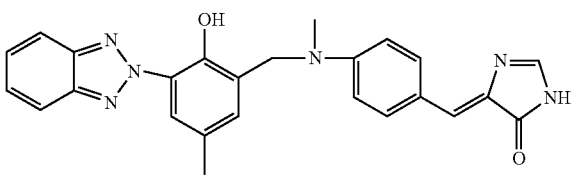

(32)

According to the method of example 4, but using compound 1,4-dihydroimidazol-5-one (CAS RN. 1968-28-1), instead of the barbituric acid compound, and compound (32) was obtained. $C_{25}H_{22}N_6O_2$, m/z: 438.2 [M]$^+$.

Example 22

4-(4-((3-(2H-benzo[d][1,2,3]triazol-2-yl)-2-hydroxy-5-methylbenzyl)(methyl)amino)ylidenebenzyl) oxazole-5-(4H)-one (Compound 33)

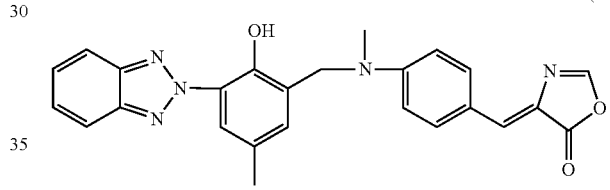

(33)

According to the method of example 4, but using compound 4H-5-oxo-oxazole (CAS RN. 497-24-5) instead of the barbituric acid compound, and compound (33) was obtained. $C_{25}H_{21}N_5O_3$, m/z: 439.2 [M]$^+$.

Example 23

3-(3-(4,6-bis(2,4-dimethylphenyl)-1,3,5-triazin-2-yl)-5-(tert-butyl)-4-hydroxyphenyl)-N-(4-((2,4,6-trioxotetrahydropyrimidine-5 (2H)-ylidene)methyl)phenyl)propionamide (Compound 34)

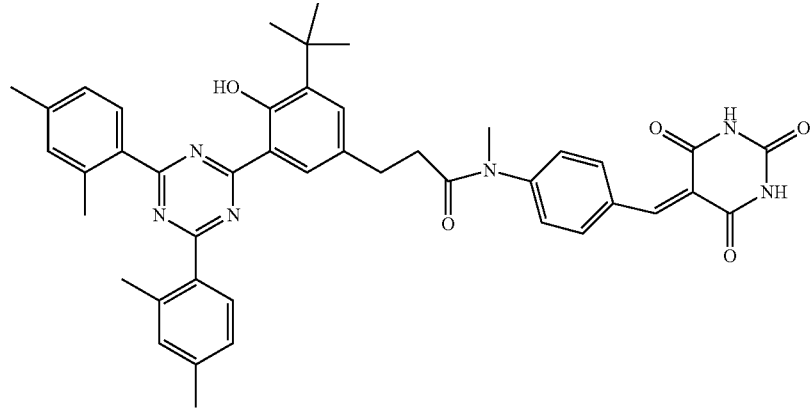

(34)

5.2 g of 3-(3-(4,6-bis(2,4-dimethylphenyl)-1,3,5-triazin-2-yl)-5-(tert-butyl)-4-hydroxybenzene Hydroxy) methyl propionate (compound 35) was dissolved in toluene, and heated to reflux in a flask equipped with a condensation trap. Compound (21) was added to the toluene solution, and samples were taken to monitor the reaction. After the reaction was completed, vacuum distillation. After chromatographic separation, compound (34) was obtained, $C_{44}H_{44}NO_5$. m/z: 736.3 $[M]^+$.

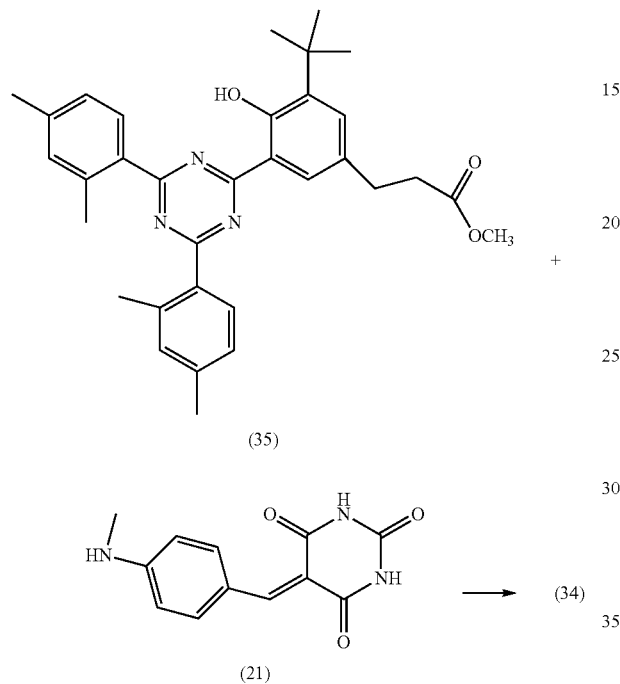

Preparation method compound (35) (according to CN201710949552.0): Briefly, 16 g of 2-chloro-4,6-bis(2',4' dimethyl-phenyl)-1,3,5-triazine (Compound 36) and 15 g of (3-tert-butyl-4-hydroxyphenyl) methyl propionate (Compound 37) are dissolved in 150 ml of chlorobenzene, and add 10 g of anhydrous aluminum trichloride. Heat and stir the mixture to dissolve. The temperature was then raised to 90° C., and samples were taken to monitor the reaction. After the completion of the reaction, the product was distilled under reduced pressure and then separated by chromatography to obtain compound (35).

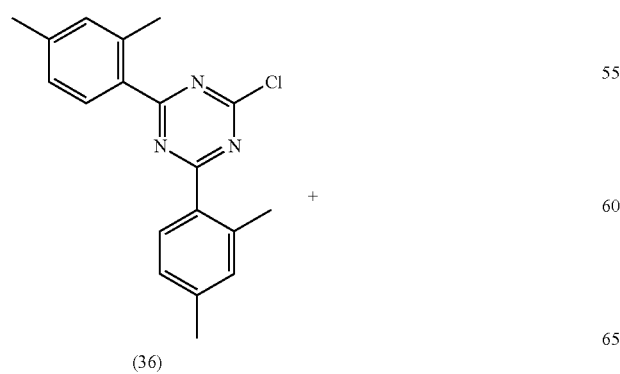

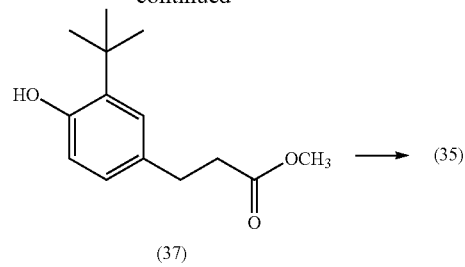

Example 24

5-(4-((3-(4,6-bis(2,4-dimethylphenyl)-1,3,5-triazin-2-yl)-5-(tert-butyl)-4-Hydroxybenzyl)amino)benzylidene)pyrimidine-2,4,6 (1H,3H,5H)-trione (Compound 38)

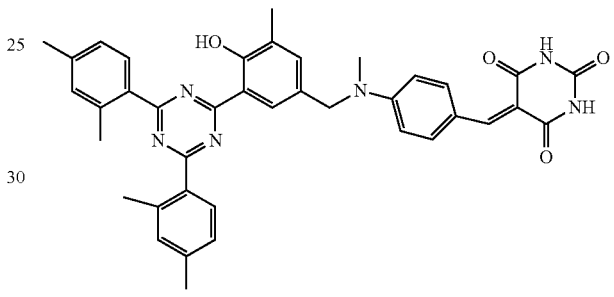

According to the method of example 13, but using 2-(4,6-bis(2,4-dimethylphenyl)-1,3,5-triazin-2-yl)-6-(tert-butyl)-4-(chloromethyl) phenol (compound 39) to replace compound (4), and the product is separated by chromatography to obtain compound (38). $C_{39}H_{36}N_6O_4$, m/z: 652.3 $[M]^+$.

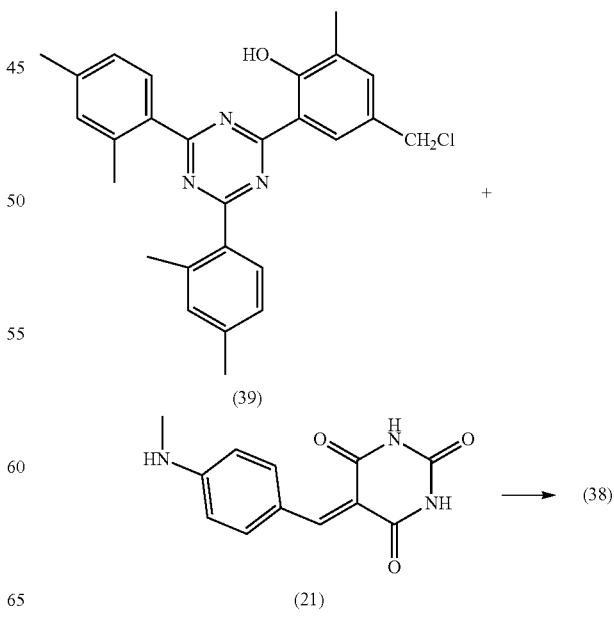

According to the preparation method of compound (35) in example 23, but 4-(chloromethyl)-2-methylphenol is used instead of (3-(tert-butyl)-4-hydroxyphenyl) methyl propionate (compound 37).

Example 25

5-(4-((5-Benzoyl-4-hydroxy-2-(octyloxy)benzyl)(methyl)amino)benzylidene)pyrimidine-2,4,6 (1H,3H,5H)-triketone (Compound 40)

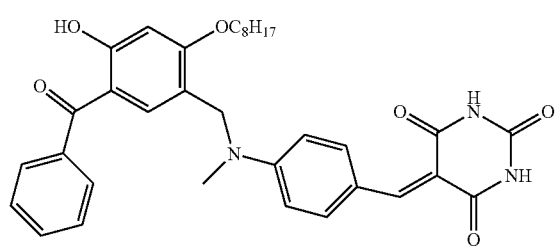

(40)

According to the method of example 13, but use (5-(chloromethyl)-2-hydroxy-4-(octyloxy)phenyl)(phenyl)methanone (compound 41) instead of compound (4). After chromatographic separation, compound (40) was obtained. $C_{34}H_{37}N_3O_6$. m/z: 583.3 [M]+.

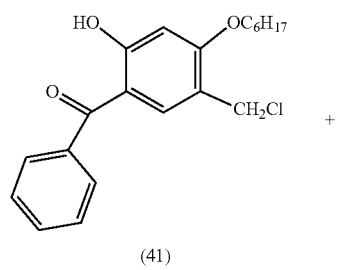

(41)

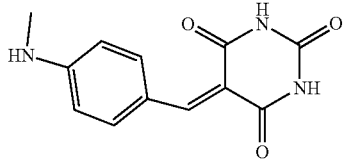

According to the method of example 1, but using (2-hydroxy-4-(octyloxy)phenyl) (phenyl) methanone (Eutec co., Eusorb UV-531) instead of UV-P (compound 3), the compound (41). was obtained.

Example 26

5-(4-(Methyl (4-(4-oxo-4H-benzo[d][1,3]azin-2-yl)benzyl)amino)benzylidene)pyrimidine-2,4, 6 (1H, 3H, 5H) triketone (compound 42)

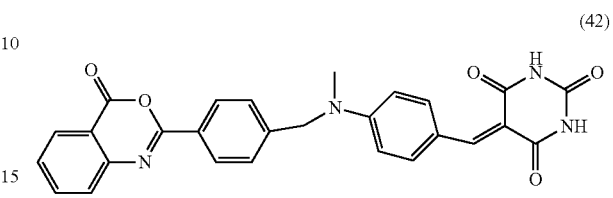

(42)

According to the method of example 13, but use 2-(chloromethyl)-4H-benzo[d][1,3]oxazin-4-one (Compound 43) instead of compound (4). After chromatographic separation, compound (42) was obtained, $C_{27}H_{20}N_4O_5$, m/z: 480.1 [M]+.

Preparation method of compound (43): Add 14 g of 2-aminobenzoic acid (compound 44) and 11 g of triethylamine to 100 ml of dichloroethane. Drop 19 g of 4-chloromethylbenzoyl chloride (compound 45) and stir and compound (43) was obtained. Preparation method of compound (45): 4-(hydroxymethyl)benzoic acid (46) was refluxed and chlorinated with thionyl chloride in dichloromethane to obtain compound (45), mp: 28° C.

Example 27

5-(4-((4-(((2,4-Dihydroxy-quinolin-3-yl)methylene)amino)benzyl)(methyl)amino)benzylidene)pyrimidine-2,4,6 (1H,3H,5H)-triketone (Compound 47)

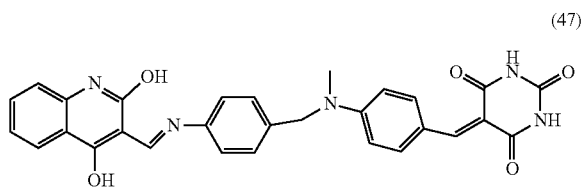 [SMILES: CN(Cc1ccc(/N=C/c2c(O)nc3ccccc3c2O)cc1)c1ccc(C=C2C(=O)NC(=O)NC2=O)cc1]
(47)

According to the method of example 13, but using 3-(((4-(chloromethyl)phenyl)imino)methyl)quinoline-2,4-diol (compound 48), instead of compound (4), the compound (47) was obtained. $C_{29}H_{23}N_5O_5$, m/z: 521.2 $[M]^+$.

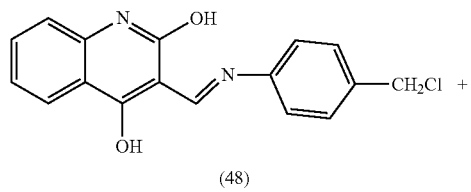
(48)

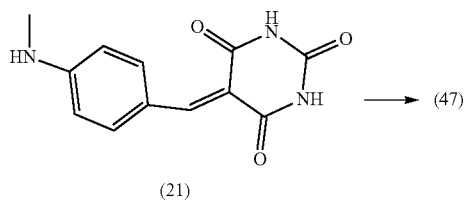
(21) → (47)

According to the method of example 1, but use 3-((benzene Subimino)methyl)quinoline-2,4-diol (UA-3701, melting point 194° C.) instead of UV-P (compound 3).

Example 28

4-(((methyl (4-((methyl (4-((2,4,6-trioxotetrahydropyrimidine-5 (2H)-ylidene)methyl)phenyl)amino) methyl)phenyl) amino) methylene) amino) ethyl benzoate (compound 49)

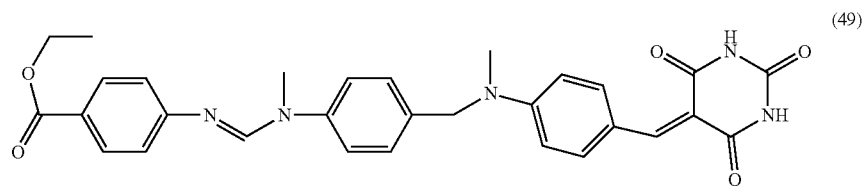 [SMILES: CCOC(=O)c1ccc(/N=C/N(C)c2ccc(CN(C)c3ccc(C=C4C(=O)NC(=O)NC4=O)cc3)cc2)cc1]
(49)

According to the method of example 13, but use 4-((((4-(chloromethyl)phenyl)(methyl)amino)methylene)amino) ethyl benzoate (compound 50), instead of (compound 4). After purification, compound (49) was obtained. $C_{30}H_{29}N_5O_5$, m/z: 539.2 $[M]^+$.

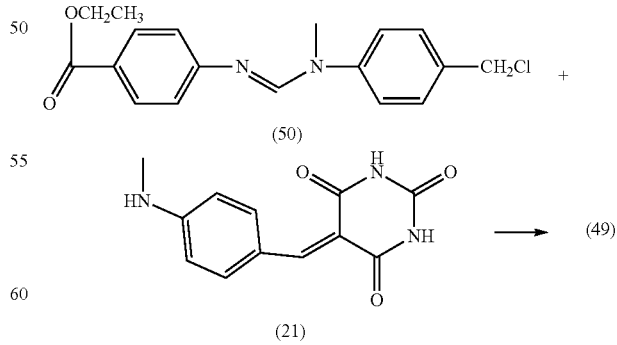
(50)

(21) → (49)

Preparation method of compound (50): According to the method of example 1, but use 4-(((methyl(phenyl)amino)methylene)amino) ethyl benzoate (UV-1, melting point 137° C.) instead of UV-P (Compound 3).

Example 29

N1-(2-ethoxy-3-((methyl (4-((2,4,6-trioxotetrahy-dropyrimidin-5 (2H)-ylidene)methyl)phenyl)amino) methyl)phenyl)-N2-(2-ethylphenyl)oxalamide (Compound 51)

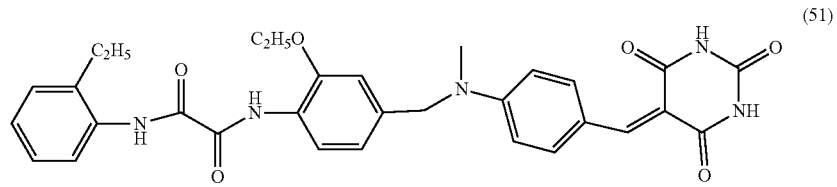

According to the method of example 13, but using N 1-(4-(chloromethyl)-2-ethoxyphenyl)-N 2-(2-ethylphenyl) oxamide (compound 52), instead of compound (4), compound (51) was obtained, $C_{31}H_{31}N_5O_6$. m/z: 569.2 [M]$^+$.

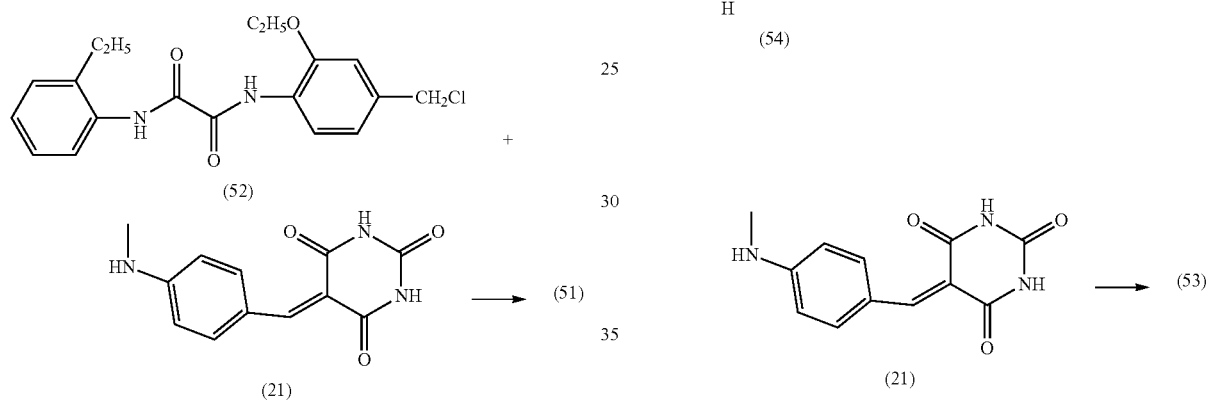

Preparation method of N 1-(4-(chloromethyl)-2-ethoxy-phenyl)-N 2-(2-ethylphenyl) oxamide (compound 52): According to example 1, but use N-(2-ethoxyphenyl)-N'-(4-ethylphenyl)-oxalamide (Eutec co., UV-312, mp: 120° C.) instead of UV-P (compound 3).

Example 30

5-(4-(((9H-carbazol-3-yl)methyl)(methyl)amino) benzylidene)pyrimidine-2,4,6 (1H,3H,5H)-trione (Compound 53)

Preparation method of 3-(chloromethyl)-9H-carbazole (compound 44): According to the method of example 1, but use 9H-carbazole instead of UV-P (compound 3).

Example 31

5-(4-(((9H-carbazol-1-yl)methyl)(methyl)amino) benzylidene)pyrimidine-2,4,6 (1H,3H,5H)-trione (Compound 55)

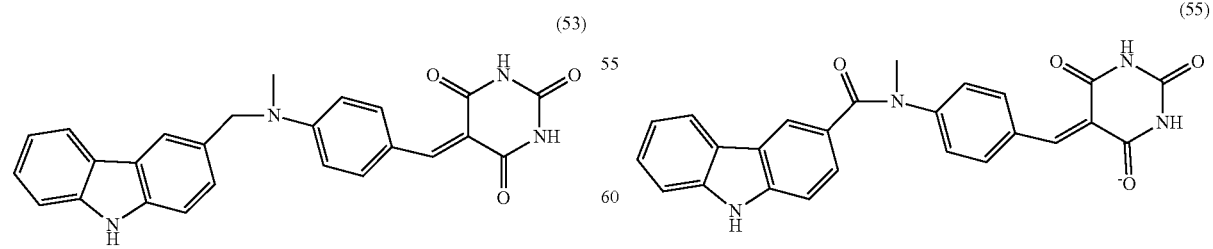

According to the method of example 13, but using 3-(chloromethyl)-9H-carbazole (compound 54), instead of compound (4), compound (53) was obtained, $C_{25}H_{20}N_4O_3$. m/z: 424.2 [M]$^+$.

According to the method of example 13, but using 9H-carbazole-3-carboxylic acid methyl ester (compound 56), instead of compound (4), compound (55) was obtained, $C_{25}H_{18}N_4O_4$, m/z: 438.1 [M]$^+$.

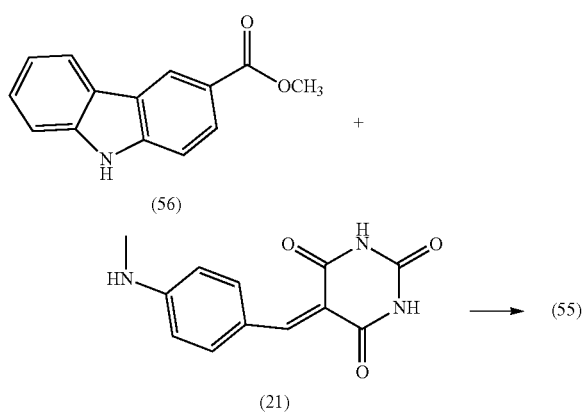

Preparation method of 9H-carbazole-1-carboxylic acid methyl ester (compound 56): 9H-carbazole-1-carboxylic acid (AKOS BC-1282), was refluxed in excess methanol using concentrated sulfuric acid as a catalyst, compound (56) was to obtained.

Example 32

5-(4-(((dibenzo[b,d]thiophen-2-ylmethyl)(methyl)amino)benzylidene)pyrimidine-2,4,6 (1H,3H,5H)-trione (Compound 57)

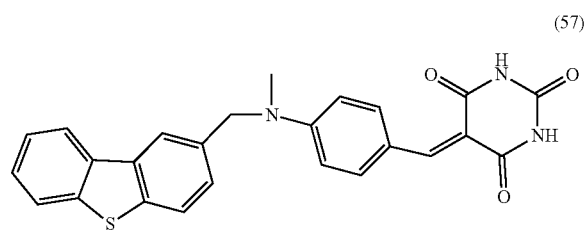 [SMILES: CN(Cc1ccc2sc3ccccc3c2c1)c1ccc(C=C2C(=O)NC(=O)NC2=O)cc1]

Method of 9H-carbazole-1-carboxylic acid methyl ester preparation: 9H-carbazole-1-carboxylic acid (AKOS BC-1282), using concentrated sulfuric acid as a catalyst, refluxed in excess methanol to obtain compound (56), $C_{25}H_{19}N_3O_3S$. m/z: 441.1 $[M]^+$.

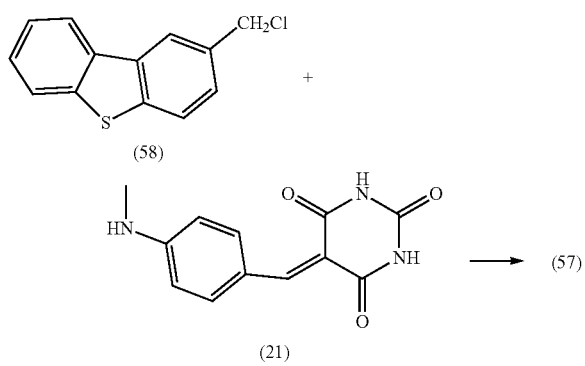

Preparation method of 2-(chloromethyl)dibenzo[b,d]thiophene (compound 58): According to the method of Example 1, but using dibenzo[b,d]thiophene instead of UV-P (Compound 3).

Example 33

Reaction mixture (59) of 2,4-di-tert-butylphenyl-3,5-di-tert-butyl-4-hydroxybenzoate (Eutec co., Eusorb UV-120) and 5-(4-(methylamino) benzylidene base) pyrimidine-2,4,6 (1H,3H,5H)-trione (compound 21)

According to the method of example 1 to 4, but using 2,4-di-tert-butylphenyl-3,5-di-tert-butyl-4-hydroxybenzoate (Eutec co., Eusorb UV-120, melting point 149° C.) instead UV-P (compound 3). UV-120 and compound (21) were refluxed in dichloromethane. The product was washed with water and dried to obtain a mixture of product (59).

Example 34

1-(3-(2H-benzo[d][1,2,3]triazol-2-yl)-2-hydroxy-5-methylbenzyl)-5-(4-(dimethylamino)benzylidene) pyrimidine-2,4-,6 (1H,3H,5H)trione (compound 60)

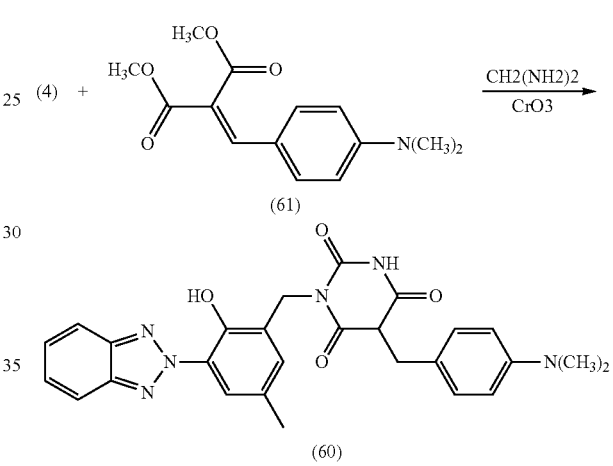

15 g of 4-(dimethylamino)benzaldehyde, 13.2 g of dimethyl malonate, and 15 ml of pyridine were dissolved in toluene and heated to reflux. Take samples to monitor the reaction, remove the solvent, and obtain dimethyl 2-(4-(dimethylamino)benzylidene) malonate (Compound 61) after chromatography. $C_{14}H_{17}NO_4$, mp: 86-88° C.

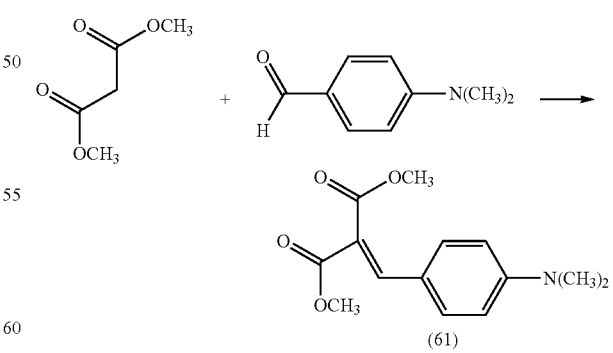

26.3 g of dimethyl 2-(4-(dimethylamino)benzylidene) malonate (Compound 61) and 4.6 g of diaminomethane were refluxed in ethanol for 3 hours. Evaporate the solvent to obtain a closed ring compound. Mix 14.6 g of the closed ring compound, 21 g of chromium trioxide, and 100 ml of water. Drop 45 ml of concentrated sulfuric acid. After dropping, add chromium trioxide (21 g/50 ml water) dropwise, and heat to reflux, take samples to monitor the reaction. After cooling to room temperature, the reaction mixture was poured into an equal volume of water and cooled to 10° C. in an ice bath. The precipitate was separated and washed with water. Disperse the precipitate in 30 ml of water, add 50 ml of saturated sodium carbonate solution and stir. Compound (60) was obtained by filtration. $C_{27}H_{24}N_6O_4$, MS: m/z=496.2 $[M]^+$.

Example 35

1-(3-(2H-benzo[d][1,2,3]triazol-2-yl)-2-hydroxy-5-methylbenzyl)-5-(4-(dimethylamino)benzylidene)-3-methylimidazolidine-2,4-dione (compound 62)

16.3 g of compound (63) and 5.1 g of 2-isocyanato-2-methylpropane were heated to reflux overnight in dichloroethane, and the unreacted 2-isocyanato-2-methylpropane was removed by distillation under reduced pressure. After 2-isocyanato-2-methylpropane and dichloroethane are separated by chromatography, 1-(3-(2H-benzo[d][1,2,3]triazol-2-yl)-2-hydroxy-5-methylbenzyl)-3-(tert-butyl) imidazolidine-2,4-dione (compound 64).

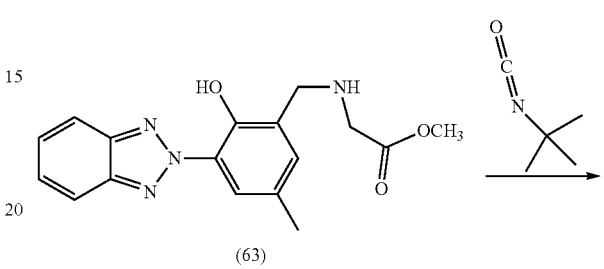

According to the method of example 2, take 27.5 g of compound (4) and add 10 g of glycine methyl ester to react to obtain (3-(2H-benzo[d][1,2,3]triazol-2-yl)-2-hydroxyl-5-methylbenzyl)glycine methyl ester (Compound 63).

According to the method of example 4, 4 g of compound (65) and 1.5 g of 4-(dimethylamino)benzaldehyde were reacted to obtain 1-(3-(2H-benzo[d][1,2,3]Triazol-2-yl)-2-hydroxy-5-methylbenzyl)-3-(tert-butyl) imidazolidine-2,4-dione (compound 62). $C_{30}H_{32}N_6O_3$, m/z: 524. 3 $[M]^+$.

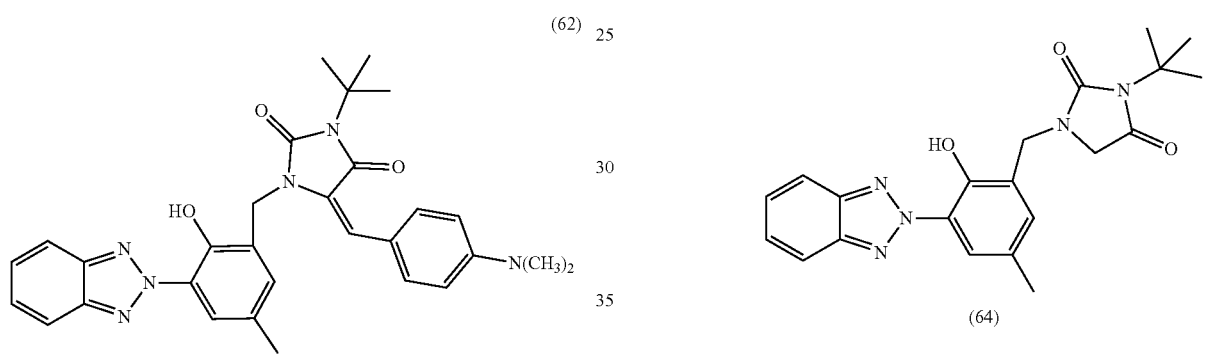

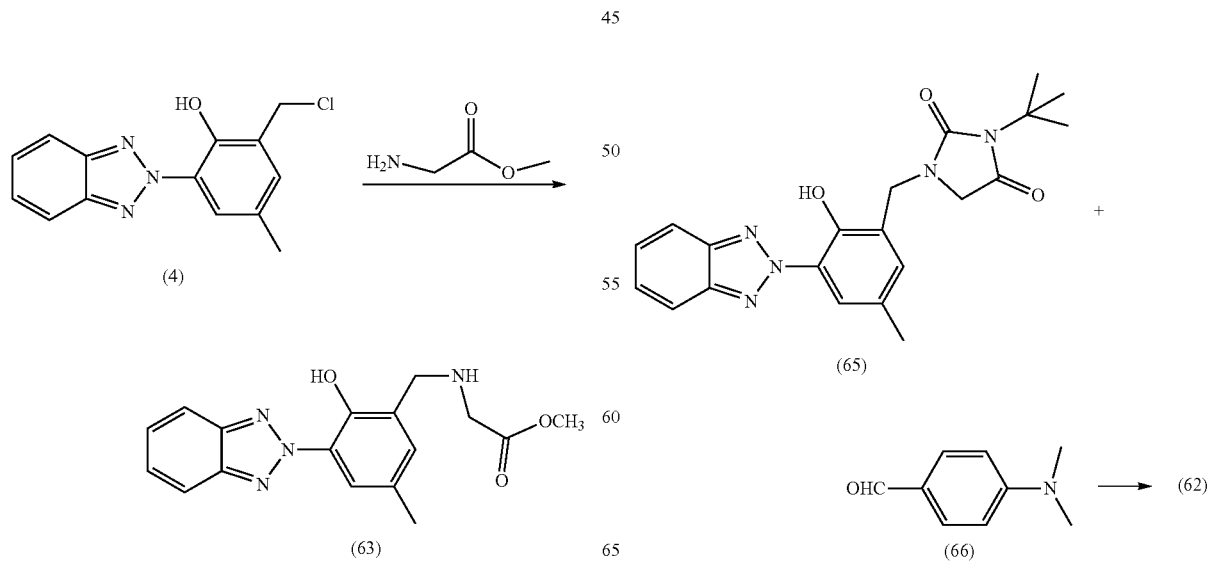

Example 36

5-(3-(2H-benzo[d][1,2,3]triazol-2-yl)-2-hydroxy-5-methylbenzyl)-2-(4-(diethylamino)phenyl)-2-methyl-1,3-dioxane-4,6-dione (compound 67) 5-(3-(2H-benzo[d][1,2,3]triazol-2-yl)-2-hydroxy-5-methylbenzylidene)-2-(4-(diethylamino)phenyl)-2-methyl-1,3-dioxane-4,6-diketone (compound 90)

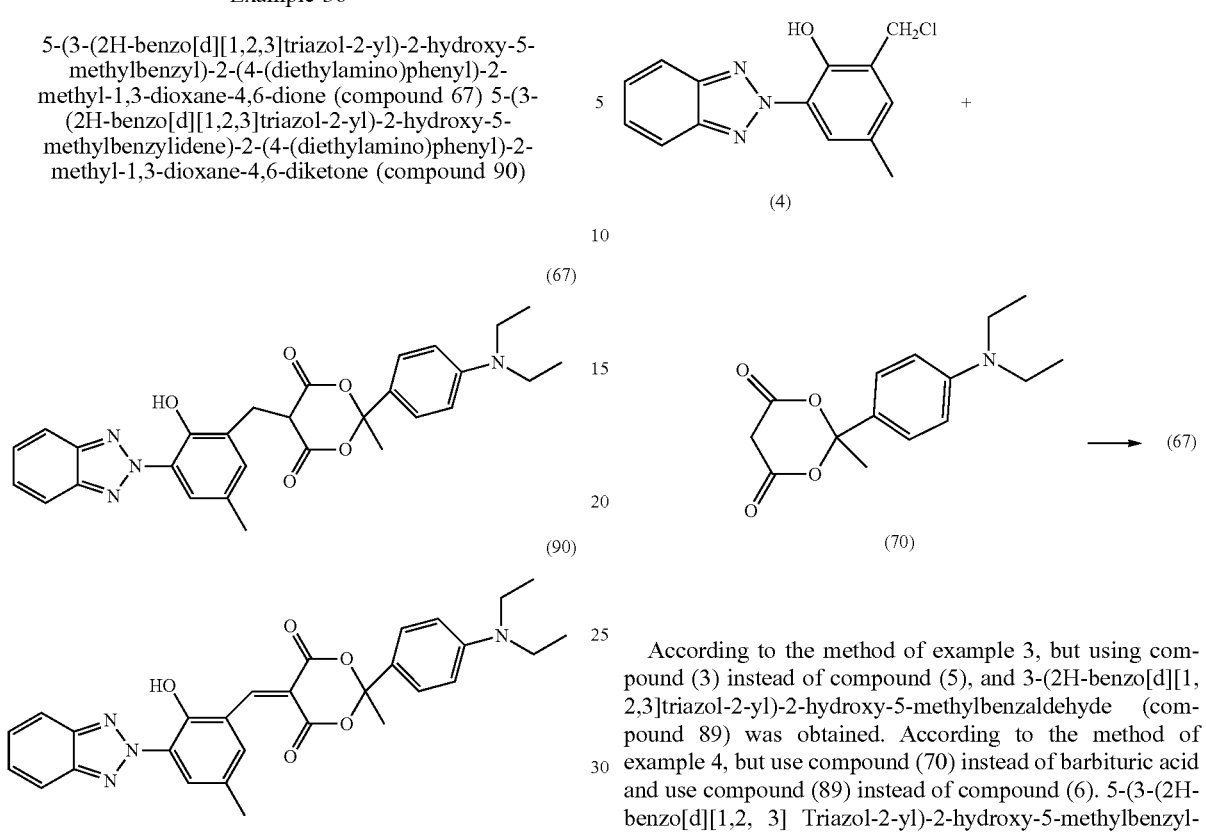

Dissolve 5.2 g of malonic acid (68) in 6 ml of acetic anhydride, add 0.15 ml of concentrated sulfuric acid with stirring in ice water. Heat the mixture to dissolve in a water bath. Add 4-(diethylamino) acetophenone (69) at room temperature and stir overnight. The product 5 was washed with water and extracted with ethyl acetate to obtain 2-(4-(diethylamino)phenyl)-2-methyl-1,3-dioxane-4,6-dione (Compound 70).

2.34 g of compound (70) and 2.75 g of compound (4) were mixed to react under reflux in ethanol solution of sodium ethoxide overnight. After removing the solvent and neutralizing with HCl, the product is separated by chromatography to obtain compound (67). $C_{29}H_{30}N_4O_5$, m/z: 514.2 $[M]^+$.

According to the method of example 3, but using compound (3) instead of compound (5), and 3-(2H-benzo[d][1,2,3]triazol-2-yl)-2-hydroxy-5-methylbenzaldehyde (compound 89) was obtained. According to the method of example 4, but use compound (70) instead of barbituric acid and use compound (89) instead of compound (6). 5-(3-(2H-benzo[d][1,2, 3] Triazol-2-yl)-2-hydroxy-5-methylbenzylidene)-2-(4-(diethylamino)phenyl)-2-methyl-1,3-dioxane-4,6-diketone (compound 90) was obtained. $C_{29}H_{28}N_4O_5$, m/z: 512.2 $[M]^+$.

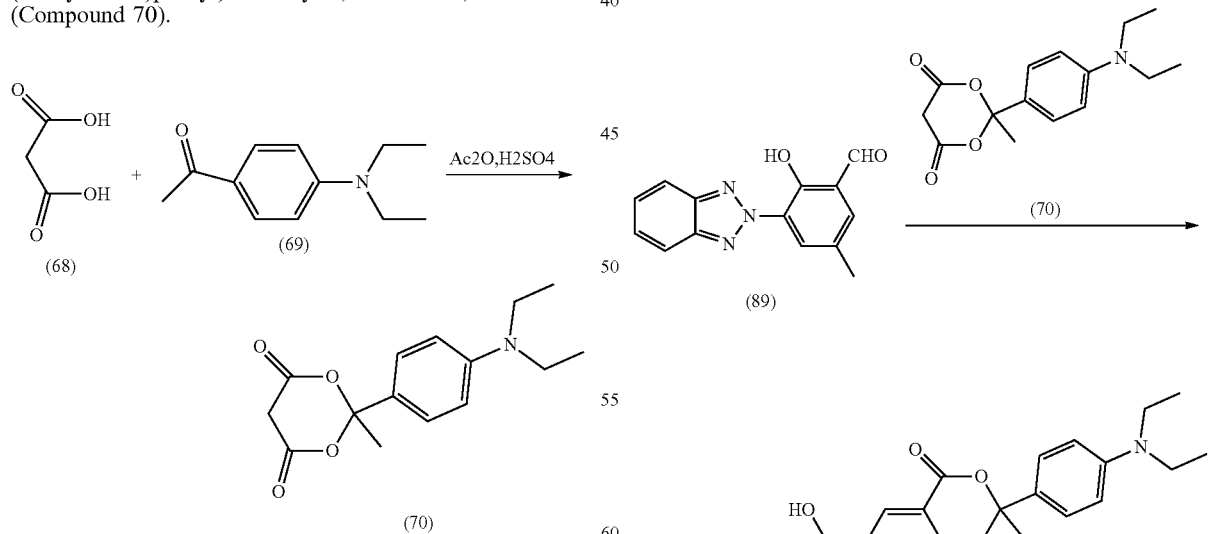

Example 37

5-(9H-carbazol-3-yl)-3-(4-(dimethylamino)phenyl) oxazolidine-2,4-dione (Compound 71)

(71)

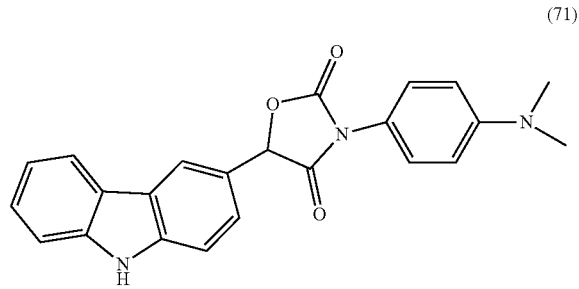 [SMILES: CN(C)c1ccc(N2C(=O)OC(c3ccc4[nH]c5ccccc5c4c3)C2=O)cc1]

Under the ice-water bath, dissolve 34 g 9H carbazole in 400 ml dry dichloromethane, slowly add 30 g anhydrous AlCl₃ and continue stirring for 10 minutes, then slowly add 31 g of 2-chloro-2-oxoacetic acid methyl esters (compound 72) and continue stirring at room temperature. Take samples for monitoring, while the reaction was completed, pour the reactant into a hydrochloric acid in ice-water bath, extract with dichloromethane, and dry to obtain methyl 2-(9H-carbazol-3-yl)-2-oxoacetate (compound 73)

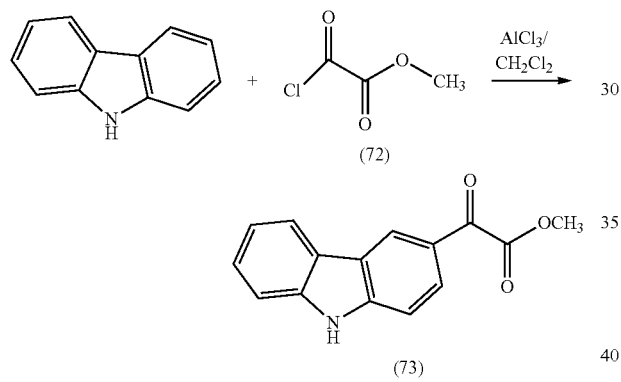

18 g of compound (73) and 150 mL of absolute ethanol were mixed and stir at room temperature. 2.6 g of sodium borohydride was added, and the reaction mixture was stirred at room temperature for 50 minutes and taken samples for monitoring. After the reaction is completed, pour the product into a hydrochloric acid in ice-water bath and extracted with ethyl acetate and dried to obtain methyl 2-(9H-carbazol-3-yl)-2-oxoacetate (Compound 74).

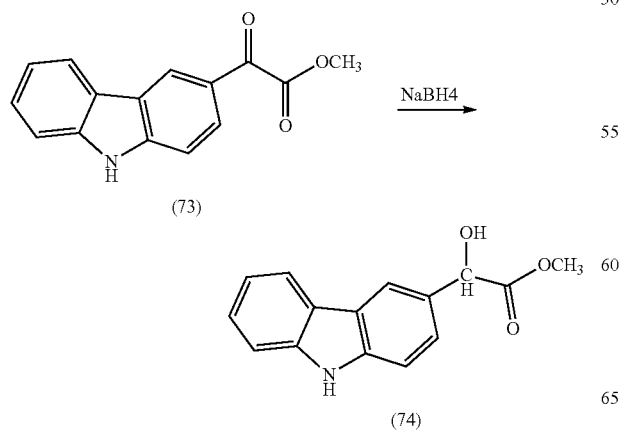

2.5 g of compound (74) was dissolved in 20 ml of dichloromethane, and 1.5 ml of triethylamine was added and stirred. 1.6 g of 4-isocyanato-N,N-dimethylaniline (75) in dichloromethane solution (10%) was added dropwise. After the addition, reflux it in dichloromethane and monitor the reaction. After the reaction was completed, neutralize it with HCl. After washing with water and evacuating the solvent, it was separated by chromatography to obtain compound (71). $C_{23}H_{19}N_3O_3$, m/z: 385.1 $[M]^+$.

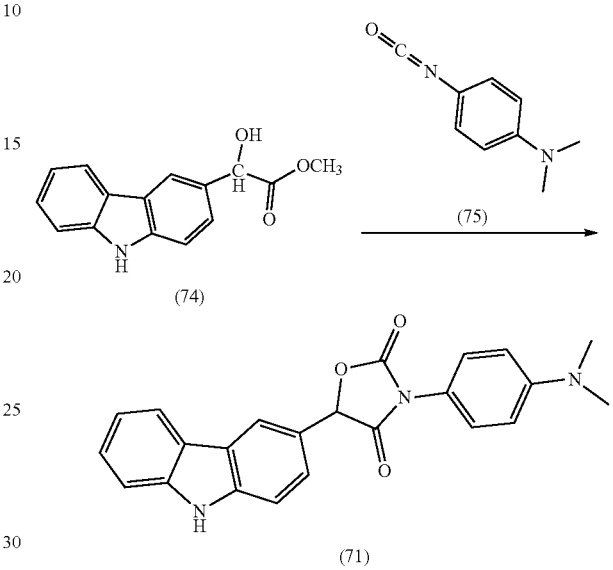

Example 38

5-((9H-carbazol-3-yl) chloromethyl)-3-(4-(dimethylamino)phenyl) oxazolidine-2,4-dione (compound 76), 5-((9H-carbazol-3-yl)methylene)-3-(4-(dimethylamino)phenyl) oxazolidine-2,4-dione (Compound 88)

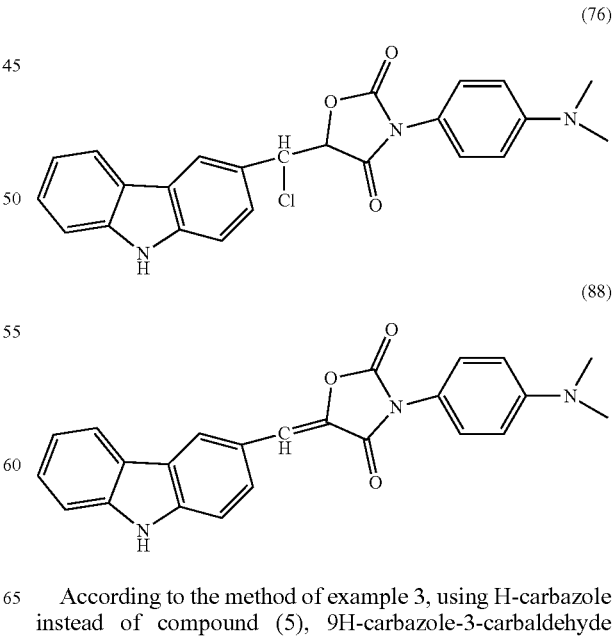

According to the method of example 3, using H-carbazole instead of compound (5), 9H-carbazole-3-carbaldehyde (compound 77) was obtained with a melting point of 158° C.

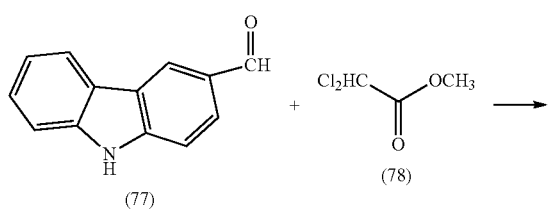

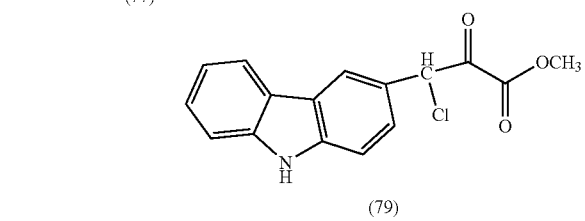

At 4° C., 5 g of 9H-carbazole-3-carbaldehyde (compound 77) and 2.5 ml of 2,2-dichloroacetic acid methyl ester were mixed in 30 ml of hydrous ether solution. Add 1.95 g of sodium methoxide under argon and keep stirring at low temperature for 1 hour, and then heated to reflux. Samples were taken to monitor. After the reaction was completed, water was added and the organic layer was separated. After drying, and chromatographic separation, methyl 3-(9H-carbazol-3-yl)-3-chloro-2-oxopropionate (79) was obtained.

According to the method of example 37, using compound (79) instead of compound (73), methyl 3-(9H-carbazol-3-yl)-3-chloro-2-hydroxypropionate (80) was obtained.

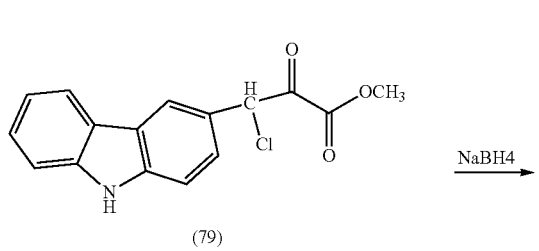

According to the method of example 37, using compound (80) instead of compound (74), methyl 3-(9H-carbazol-3-yl)-3-chloro-2-hydroxypropionate (76) was obtained. $C_{24}H_{20}ClN_3O_3$, m/z: 433.1 $[M]^+$.

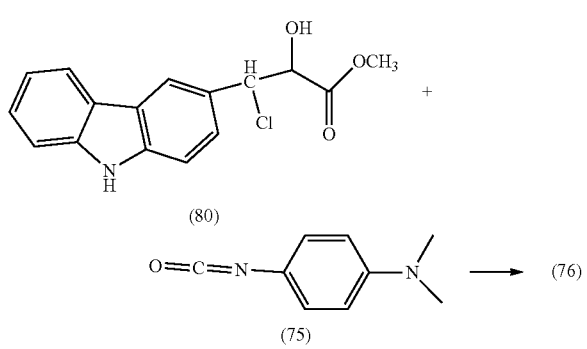

4.3 g of compound (76) was dissolved in pyridine and heated to 80° C. Add 1.5 ml of DBU (1,8-diazabicycloundec-7-ene) to react. After the completion of the reaction (sampling monitoring), distillation was performed under reduced pressure. After chromatographic separation, compound (88) is obtained. $C_{24}H_{19}N_3O_3$, m/z: 397.1 $[M]^+$.

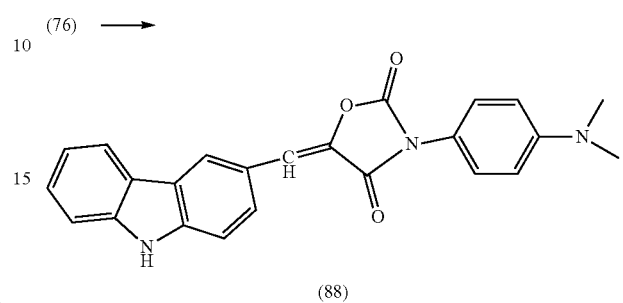

Example 39

2-(1-(9H-carbazol-3-yl)ethyl)-5-(4-(dimethylamino)benzylidene)-1,3-dioxane-4,6-dione (compound 81)

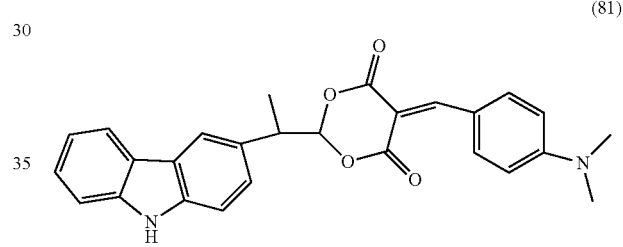

In an ice-water bath, dissolve 34 g of 9H-carbazole in dichloromethane, then slowly add 30 g of anhydrous $AlCl_3$ and continue stirring for 10 minutes, and then slowly add 20 ml of acetyl chloride dropwise. After the addition was complete, continue stirring at room temperature. After the reaction is completed, the reaction solution was slowly poured into a hydrochloric acid in ice-water bath, extracted with dichloromethane, concentrated and separated by chromatography to obtain the main product, 3-acetylcarbazole (82), with a melting point of 167° C.

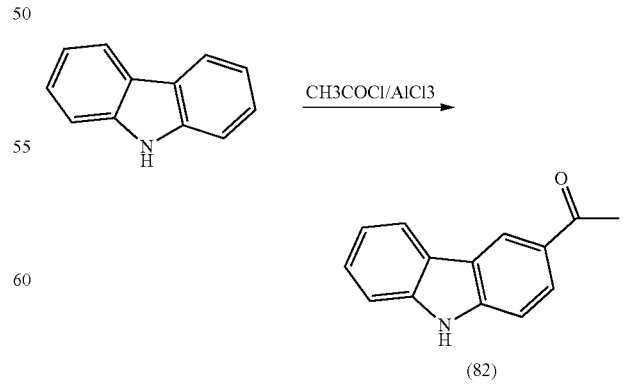

Heat 5.2 g of malonic acid, 15.3 g of acetic anhydride, and 0.2 ml of concentrated sulfuric acid in a water bath. After cooling to room temperature, 8.4 g of 3-acetylcarbazole (82) was added dropwise and kept for 1 hour, then placed in a refrigerator overnight. After washing with water, it was extracted with ethyl acetate and separated by chromatography to obtain 2-(1-(9H-carbazol-3-yl)ethyl)-1,3-dioxane-4,6-dione (83).

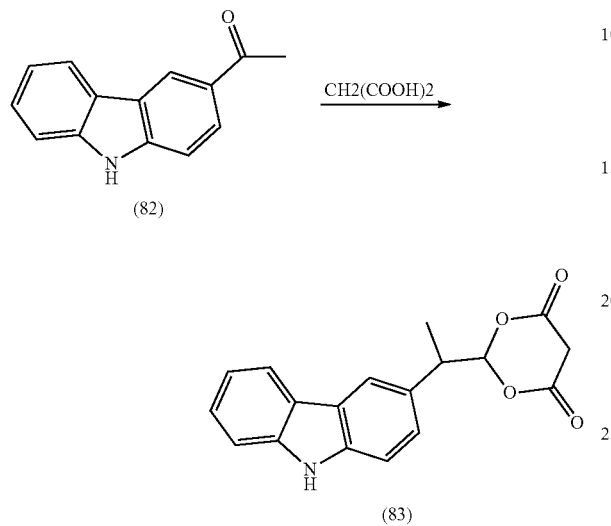

According to the method of example 35, but using compound (83) instead of compound (65), compound (81) was obtained. $C_{27}H_{24}N_2O_4$, m/z: 440.2 $[M]^+$.

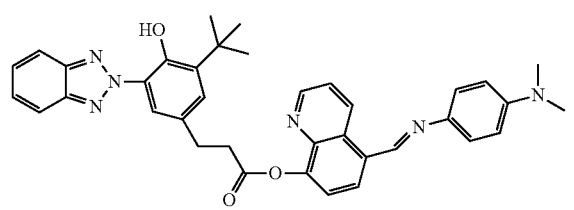

Example 40

5-(((4-(Dimethylamino)phenyl)imino)methyl)quinolin-7-yl-3-(3-(2H-benzo[d][1,2,3]triazole-2-yl) tert-butyl)-4-hydroxyphenyl) propionate (compound 84)

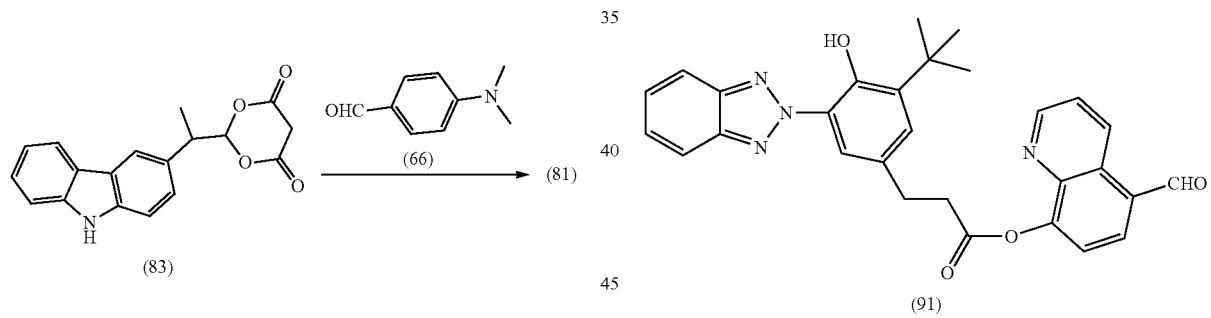

Methyl 3-(3-(2H-benzo[d][1,2,3]triazol-2-yl)-5-(tert-butyl)-4-hydroxyphenyl) propionate (Eutec co., BZTME, compound 85), hydrolyzed in KOH/MeOH, and then neutralized by adding acid. Extract with dichloromethane to obtain 3-(3-(2H-benzo[d][1,2,3]triazol-2-yl)-5-(tert-butyl)-4-hydroxyphenyl) propane diacid (86). After fully drying, add excess thionyl chloride, heat to reflux. After the reaction was completed (sampling for confirmation), evaporate the unreacted thionyl chloride to obtain the compound 3-(3-(2H-benzo[d][1,2,3]Triazol-2-yl)-5-(tert-butyl)-4-hydroxyphenyl) propionyl chloride for further use.

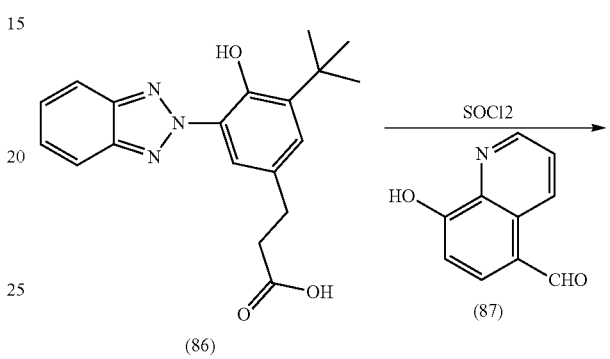

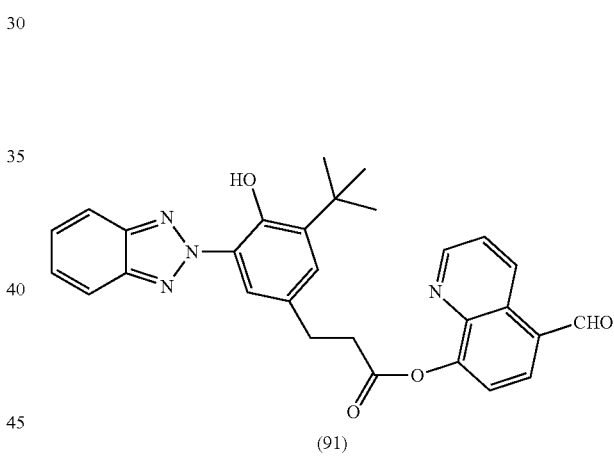

1.75 g of 8-hydroxyquinoline-5-carbaldehyde (NSC 122131, compound 87) was dissolved in 20 ml of dichloromethane, and 2 g of triethylamine was added and stirred. Drop 3.6 g of the aforementioned 3-(3-(2H-benzo[d][1,2,3]triazol-2-yl)-5-(tert-butyl)-4-hydroxyphenyl) propionyl chloride dichloromethane solution (20 ml) of compound (86). Stir overnight at room temperature. The product was poured into ice water, extracted with dichloromethane, and washed with 1% dilute hydrochloric acid and brine. After drying, the compound 5-formylquinolin-8-yl 3-(3-(2H-benzo[d][1,2,3]triazol-2-yl)-5-(tert-butyl)-4-Hydroxyphenyl)propionate (91).

5 g of compound (91) and 1.4 g of p-(dimethylamino)aniline were dissolved in 40 ml of absolute ethanol and heated to reflux for 4 hours. Sample was taken to monitor. After the reaction was completed, the solvent was removed to obtain compound (84). $C_{37}H_{36}N_6O_3$, m/z: 612.3 $[M]^+$.

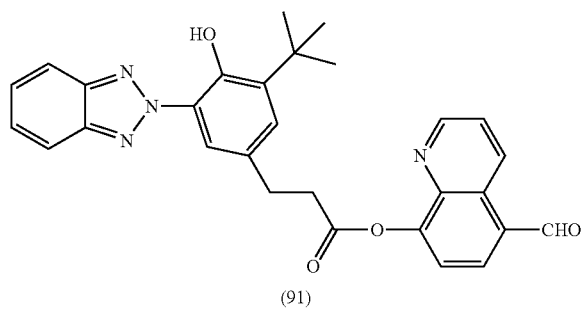

(91)

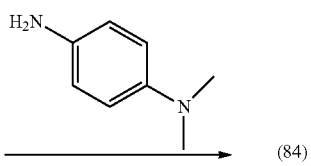

(84)

Example 41

The improvement of the performance on optical recording media: after covalent bonding, compound (18) was synthesized from compound (B) as shown in the figure below.

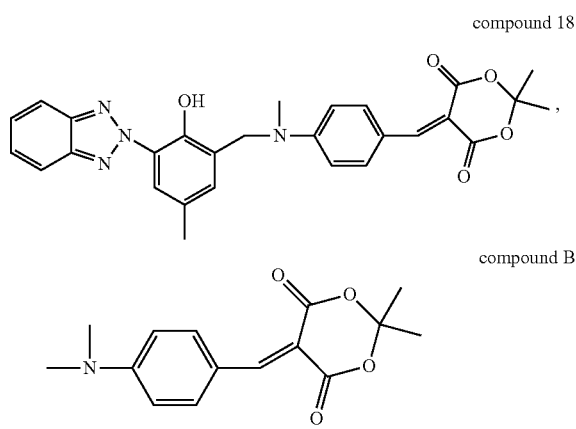

compound 18 compound B

The melting point of compound (B) is 175° C. After covalent bonding with benzotriazole compounds, the melting point raises to 224° C. (compound 18). This is an important improvement for organic dyes (B) used in optical recording media. This is because compound (18) is less likely to decompose under the high temperature (250° C. or above) generated locally by laser irradiating the disc.

Figure 3:
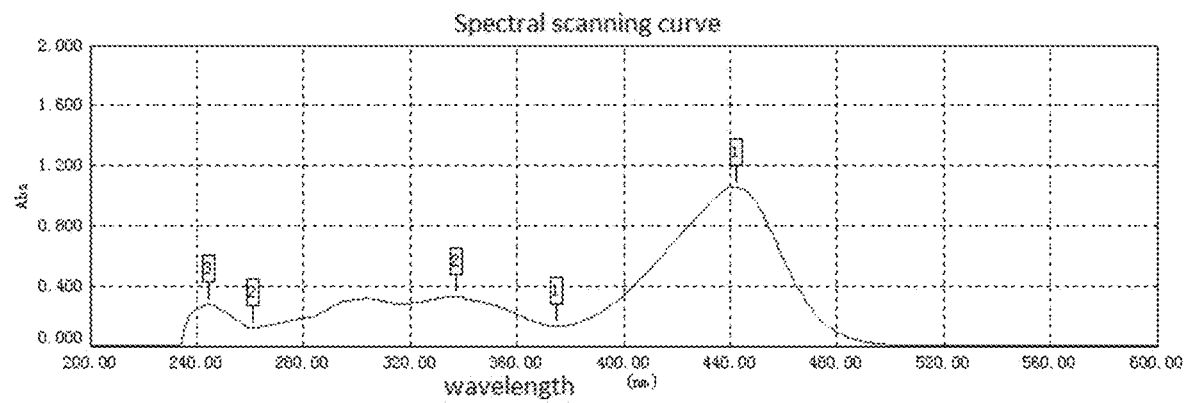
FIG. 3, UV-VIS absorption of compound (18) of the present invention (10 mg/tetrahydrofuran)

FIG. 3 illustrates the UV absorption range of compound (18), covering UVA, UVB and blue light. This indicates that the dye of compound (18) can provide a wide range of ultraviolet light (UVA+UVB) protection for optical discs. Therefore, compared with compound (B), compound (18) is more advantageous in the storage of optical discs.

TABLE 3

Comparison of compound (B) and compound (18)

| | compound (B) | compound (18) of the present invention |
|---|---|---|
| Heat properties | Mp 175° C. | Mp 224° C. |
| Absorption range | UVA + visible light | UVA + UVB + visible light |

Example 42

Advantages of being used in ultraviolet light or blue light absorbers: when the compound of the present invention is used in ultraviolet light and/or blue light absorbers, it has both ultraviolet light (UVA+UVB) and blue light absorption functions. Compared with the commercial anti-blue light agent, Eusorb UV-1990 (Eutec co.), (Table 4) it shows that the commercial product Eusorb UV-1990 has weak absorption of UVB (wavelength 280 nm). The example compound of the present invention has better coverage and absorption of ultraviolet light than the currently commercially available anti-blue light agent Eusorb UV-1990.

TABLE 4

Comparison of the title compounds of the examples and the commercially available Eusorb UV-1990 anti-blue light agent

| | Abs | |
|---|---|---|
| | UVB(about 280 nm) | Blue light(about 390 nm) |
| Title compounds of examples 4-40 | >0.2 | >0.9 |
| Commercial available anti-blue light agent Eusorb UV-1990 | <0.05 | >0.8 |

Example 43

Figure 2:
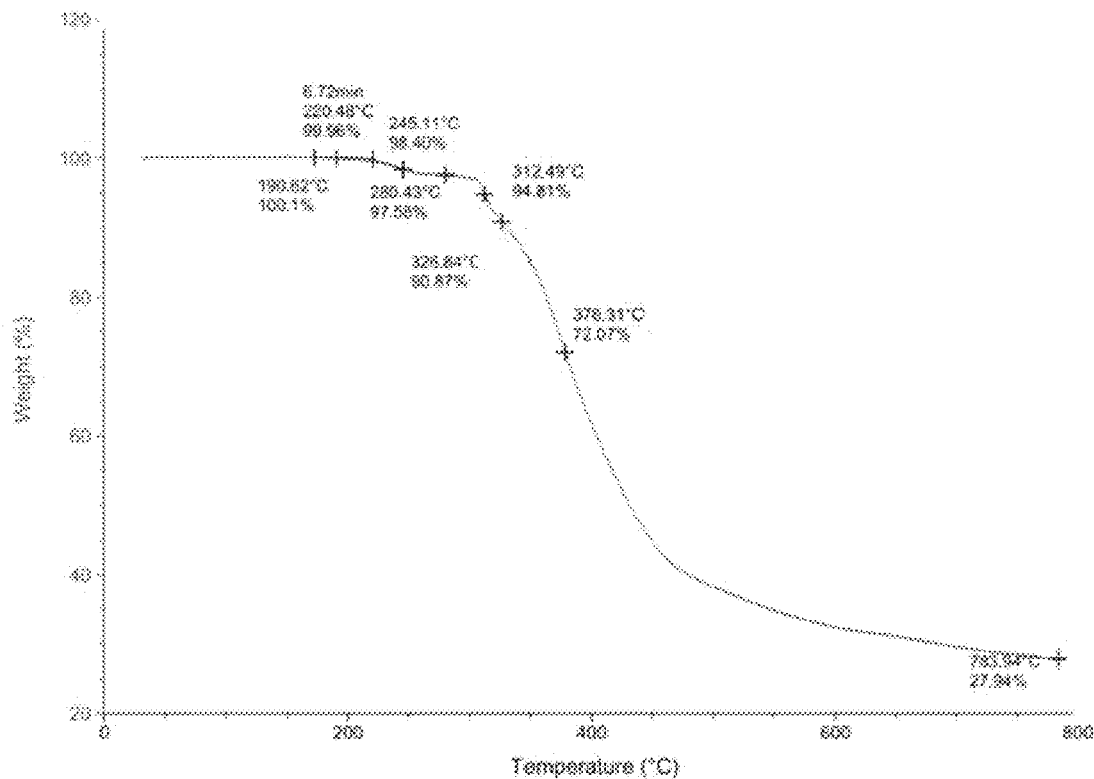
FIG. 2, TGA (thermogravimetric analyzer) diagram of the compound (7) of the present invention.

Stability and weather resistance of the light conversion agent: Thermogravimetric analyzer (TGA) was used to measure the thermal stability of the example compounds. The greater the weight loss, the worse the stability is. FIG. 2 shows the results of TGA: when the temperature is increased to 220° C., the weight loss of compound (7) of example 4 is less than 1%. Rising to 312° C., the weight loss is only about 5%. This shows that compound (7) has very high thermal stability.

Figure 4:
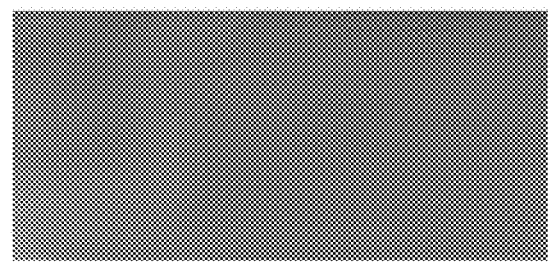
FIG. 4 The appearance of the agricultural film made of the light conversion agent of the present invention.

FIG. 4 is a photograph of the PE agricultural film made of compound (7) of example 4 of the present invention under a fluorescent lamp (to show the color, the agricultural film is placed on a gray opaque background). The agricultural film is transparent and orange-red. Table 5 shows the comparison of the weather resistance before and after the modification of RL1000. The RL1000 product (BASF) can only maintain the stability of two seasons when used in outdoor agricultural film, while the compound (7) of the present invention is more than three seasons.

TABLE 5

Comparison of weather resistance

| | RL1000 | compound(7) |
|---|---|---|
| weather resistance | two seasons | three seasons |
| Emission | about 600-700 nm | about 600-700 nm |

The present invention has been disclosed in preferred embodiments above, but it is not intended to limit the present invention. All technical solutions obtained by equivalent substitutions or equivalent changes fall within the protection scope of the present invention.

What is claimed is:

1. A novel type of polycyclic compound, a structure of the compound is represented by formula (1), $$A\text{-}R_1\text{—}B\text{—}R_2\text{—}C\text{—}R_3\text{-}D \qquad (1),$$

wherein, A-R$_1$—B is

[structure]

$R_2$ is —(CHR$_{21}$)$_q$ N(R$_{22}$)—, R$_{21}$ and R$_{22}$ are each independently hydrogen, or linear or branched C$_1$~C$_8$ alkyl;

q=1;

C is a benzene ring,

R$_3$ is —C(R$_{16}$)=, R$_{16}$ is selected from the group consisting of hydrogen, linear or branched C$_1$~C$_6$ alkyl, and phenyl substituted with C$_1$~C$_4$ alkyl, R$_4$ is one or more selected from the group consisting of hydrogen, halogen, hydroxyl, C$_1$~C$_4$ alkoxy, and linear or branched C$_1$~C$_8$ alkyl, p=0~2, R$_{19}$ is hydrogen, or linear or branched C$_1$~C$_6$ alkyl, D is

[structures], or [structure],

R$_9$, R$_{25}$~ and R$_{26}$ are each independently hydrogen, or linear or branched C$_1$~C$_6$ alkyl R$_2$—C—R$_3$-D R$_2$-D R$_3$—C A-R$_1$-B.

2. The compound according to claim 1, wherein,

[structures]

the compound is selected from the group consisting of:

(7)

[structure]

(8)

[structure]

(9)

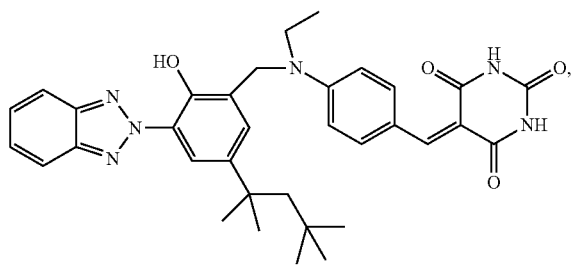

(12)

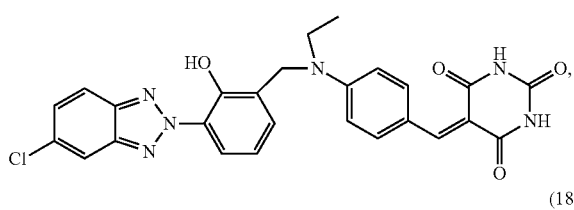

(18)

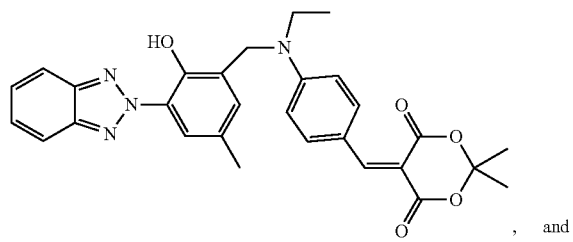

, and (19)

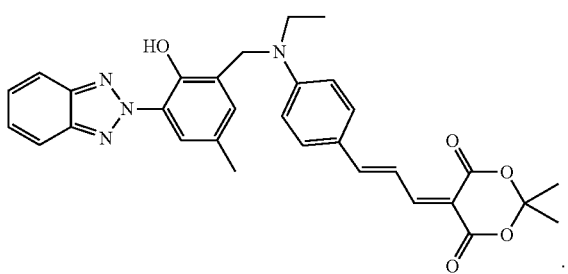

3. A film, which comprises one or more additives including light conversion agent, dye, pigment, fluorescence agent, ultraviolet light absorber or blue light absorber, a structure of the additive is represented by formula (1) of according to claim 1.

4. A film, which comprises one or more additives including light conversion agent, dye, pigment, fluorescence agent, ultraviolet light absorber or blue light absorber, a structure of the additive is represented by formula (1) according to claim 2.

* * * * *